(12) United States Patent
Keusenkothen et al.

(10) Patent No.: US 9,868,680 B2
(45) Date of Patent: *Jan. 16, 2018

(54) METHOD AND APPARATUS FOR CONVERTING HYDROCARBONS INTO OLEFINS

(75) Inventors: Paul F. Keusenkothen, Houston, TX (US); Frank Hershkowitz, Basking Ridge, NJ (US); Jason D. Davis, Humble, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 272 days.

This patent is subject to a terminal disclaimer.

(21) Appl. No.: 13/993,522

(22) PCT Filed: Dec. 20, 2011

(86) PCT No.: PCT/US2011/066202
§ 371 (c)(1),
(2), (4) Date: Sep. 18, 2013

(87) PCT Pub. No.: WO2012/099677
PCT Pub. Date: Jul. 26, 2012

(65) Prior Publication Data
US 2014/0303339 A1    Oct. 9, 2014

Related U.S. Application Data

(60) Provisional application No. 61/434,410, filed on Jan. 19, 2011, provisional application No. 61/434,411, filed on Jan. 19, 2011, provisional application No. 61/434,409, filed on Jan. 19, 2011, provisional application No. 61/434,415, filed on Jan. 19, 2011, provisional application No. 61/434,417, filed on Jan.

(Continued)

(30) Foreign Application Priority Data
Mar. 31, 2011   (EP) .................................. 11160758

(51) Int. Cl.
*C07C 4/04*    (2006.01)
*C07C 2/06*    (2006.01)
(Continued)

(52) U.S. Cl.
CPC .................. *C07C 4/04* (2013.01); *C07C 2/76* (2013.01); *C08F 110/02* (2013.01);
(Continued)

(58) Field of Classification Search
CPC .... C07C 4/04; C07C 2/78; C07C 5/09; C10G 9/00; C10G 9/002; C10G 9/007;
(Continued)

(56) References Cited

U.S. PATENT DOCUMENTS

| | | |
|---|---|---|
| 1,134,677 A | 4/1915 | Heinemann |
| 1,860,624 A | 5/1932 | Sauerwein |

(Continued)

FOREIGN PATENT DOCUMENTS

| | | |
|---|---|---|
| BE | 722895 | 10/1968 |
| DE | 875198 | 4/1953 |

(Continued)

OTHER PUBLICATIONS

Energy Fuels, 2007, 21(2), pp. 640-645.
(Continued)

*Primary Examiner* — In Suk Bullock
*Assistant Examiner* — Philip Louie

(57) ABSTRACT

An apparatus and method are provided for processing hydrocarbon feeds. The method enhances the conversion of hydrocarbon feeds into conversion products, such as ethylene and propylene. In particular, the present techniques utilize a high-severity reactor integrated with another reactor type to convert hydrocarbons to other petrochemical products.

14 Claims, 10 Drawing Sheets

Related U.S. Application Data 19, 2011, provisional application No. 61/434,419, filed on Jan. 19, 2011, provisional application No. 61/434,413, filed on Jan. 19, 2011, provisional application No. 61/481,999, filed on May 3, 2011, provisional application No. 61/500,854, filed on Jun. 24, 2011, provisional application No. 61/504,611, filed on Jul. 5, 2011.

(51) Int. Cl.

| | | |
|---|---|---|
| *C08F 110/02* | (2006.01) | |
| *C08F 110/06* | (2006.01) | |
| *C10G 9/00* | (2006.01) | |
| *C10G 9/16* | (2006.01) | |
| *C10G 9/18* | (2006.01) | |
| *C10G 9/26* | (2006.01) | |
| *C10G 9/38* | (2006.01) | |
| *C07C 2/76* | (2006.01) | |

(52) U.S. Cl.
 CPC .............. *C08F 110/06* (2013.01); *C10G 9/00* (2013.01); *C10G 9/002* (2013.01); *C10G 9/007* (2013.01); *C10G 9/16* (2013.01); *C10G 9/18* (2013.01); *C10G 9/26* (2013.01); *C10G 9/38* (2013.01)

(58) Field of Classification Search
 CPC ... C10G 9/16; C10G 9/18; C10G 9/26; C10G 9/38; C08F 110/06; C08F 110/02
 USPC ....... 585/310, 324, 329, 330, 539, 540, 541, 585/648, 650, 651, 652; 526/348, 351, 526/352; 422/600, 620, 650
 See application file for complete search history.

(56) References Cited

U.S. PATENT DOCUMENTS

| | | |
|---|---|---|
| 2,319,679 A | 5/1943 | Hasche et al. |
| 2,678,339 A | 5/1954 | Harris |
| 2,692,819 A | 10/1954 | Hasche et al. |
| 3,024,094 A | 3/1962 | Coberly |
| 3,093,697 A | 6/1963 | Kasbohm et al. |
| 3,156,733 A | 11/1964 | Happel et al. |
| 3,242,223 A | 3/1966 | Nonnenmacher et al. |
| 3,258,455 A | 6/1966 | Natta et al. |
| 3,268,615 A * | 8/1966 | Keenan, III .............. C07C 4/04 585/635 |
| 3,305,538 A | 2/1967 | Natta et al. |
| 3,364,190 A | 1/1968 | Emrick |
| 3,419,632 A | 12/1968 | Sogawa et al. |
| 3,617,495 A | 11/1971 | Zimmerman, Jr. et al. |
| 3,644,555 A | 2/1972 | Nagy et al. |
| 3,645,992 A | 2/1972 | Elston |
| 3,796,768 A * | 3/1974 | Starzenski .............. B41J 25/24 208/54 |
| 3,839,484 A | 10/1974 | Zimmerman, Jr. et al. |
| 4,076,698 A | 2/1978 | Anderson et al. |
| 4,243,691 A | 1/1981 | Mohlenkamp, Jr. et al. |
| 4,274,841 A | 6/1981 | Andresen et al. |
| 4,302,565 A | 11/1981 | Goeke et al. |
| 4,508,842 A | 4/1985 | Beran et al. |
| 4,659,685 A | 4/1987 | Coleman, III et al. |
| 4,956,426 A | 9/1990 | Ardell et al. |
| 5,102,841 A | 4/1992 | Cann et al. |
| 5,238,892 A | 8/1993 | Chang |
| 5,280,074 A | 1/1994 | Schreck et al. |
| 5,288,473 A | 2/1994 | Shaw et al. |
| 5,364,915 A | 11/1994 | Benham et al. |
| 5,675,041 A | 10/1997 | Kiss et al. |
| 5,856,592 A | 1/1999 | Hagen |
| 5,892,079 A | 4/1999 | Wilson, Jr. |
| 5,960,643 A | 10/1999 | Kuechler et al. |
| 6,049,011 A | 4/2000 | Kiss et al. |
| 6,111,156 A * | 8/2000 | Oballa et al. ................. 585/330 |
| 6,121,503 A | 9/2000 | Janssen et al. |
| 6,177,600 B1 | 1/2001 | Netzer |
| 6,210,561 B1 | 4/2001 | Bradow et al. |
| 6,307,093 B1 | 10/2001 | Godwin et al. |
| 6,578,378 B2 | 6/2003 | Kaiser et al. |
| 6,822,057 B2 | 11/2004 | Rodgriguez |
| 7,045,583 B2 | 5/2006 | Kuchta et al. |
| 7,045,670 B2 | 5/2006 | Johnson et al. |
| 7,115,789 B2 | 10/2006 | Kuechler et al. |
| 7,119,240 B2 | 10/2006 | Hall et al. |
| 7,138,047 B2 | 11/2006 | Stell et al. |
| 7,208,647 B2 * | 4/2007 | Peterson et al. ............. 585/324 |
| 7,354,979 B2 | 4/2008 | Brant et al. |
| 7,491,250 B2 | 2/2009 | Hershkowitz et al. |
| 7,728,084 B2 | 6/2010 | Hagerty et al. |
| 7,815,873 B2 | 10/2010 | Sankaranarayanan et al. |
| 7,846,401 B2 | 12/2010 | Hershkowitz et al. |
| 7,914,667 B2 | 3/2011 | Keusenkothen et al. |
| 7,943,808 B2 | 5/2011 | Hershkowitz et al. |
| 7,976,797 B2 | 7/2011 | Chun et al. |
| 8,106,248 B2 | 1/2012 | Keusenkothen et al. |
| 8,158,837 B2 | 4/2012 | Mamadov et al. |
| 8,278,231 B2 | 10/2012 | Chun et al. |
| 8,440,070 B2 | 5/2013 | Keusenkothen |
| 8,512,663 B2 | 8/2013 | Chun et al. |
| 8,821,806 B2 | 9/2014 | Hershkowitz et al. |
| 8,932,534 B2 | 1/2015 | Chun et al. |
| 9,346,728 B2 | 5/2016 | Keusenkothen et al. |
| 2002/0000085 A1 | 1/2002 | Hall et al. |
| 2002/0098430 A1 | 7/2002 | Kawamura et al. |
| 2004/0002553 A1 | 1/2004 | Hall et al. |
| 2004/0192982 A1 | 9/2004 | Kuechler et al. |
| 2007/0090018 A1 | 4/2007 | Keusenkothen et al. |
| 2007/0090019 A1 | 4/2007 | Keusenkothen et al. |
| 2007/0090020 A1 | 4/2007 | Buchanan et al. |
| 2007/0191664 A1 * | 8/2007 | Hershkowitz et al. ........ 585/539 |
| 2008/0142049 A1 | 6/2008 | Onishi et al. |
| 2008/0300438 A1 * | 12/2008 | Keusenkothen et al. ..... 585/400 |
| 2010/0130803 A1 | 5/2010 | Keusenkothen et al. |
| 2010/0290978 A1 * | 11/2010 | Chun ....................... B01J 4/002 423/445 R |
| 2010/0292523 A1 | 11/2010 | Hershkowitz et al. |

FOREIGN PATENT DOCUMENTS

| | | |
|---|---|---|
| DE | 1270537 | 6/1968 |
| DE | 2354217 | 5/1975 |
| EP | 0 012 147 B | 5/1985 |
| EP | 0 612 753 A | 2/1994 |
| EP | 1288182 | 3/2003 |
| EP | 1741691 | 1/2007 |
| EP | 2022772 | 2/2009 |
| GB | 795688 | 5/1958 |
| GB | 834419 | 5/1960 |
| GB | 846679 | 8/1960 |
| GB | 1007423 | 10/1965 |
| GB | 1090983 | 11/1967 |
| WO | 2005/097948 | 10/2005 |
| WO | 2011/008389 | 1/2011 |
| WO | 2012/099679 | 7/2012 |

OTHER PUBLICATIONS

Watt, L., "The Production of Acetylene from Methane by Partial Oxidation", Thesis University OG British Columbia, Sep. 1, 1951, pp. 1-50.
SRI Consulting Process Economics Program "Acetylene" Report 16 (1966) and 16A (1982).
U.S. Appl. No. 61/349,464, Hershkowitz et al., filed May 28, 2010.
U.S. Appl. No. 61/226,499, Keusenkothen, filed Jul. 17, 2009.

* cited by examiner

METHOD AND APPARATUS FOR CONVERTING HYDROCARBONS INTO OLEFINS

CROSS-REFERENCE TO RELATED APPLICATIONS

This application claims priority from (i) U.S. Provisional Application Ser. No. 61/434,410, filed Jan. 19, 2011, EP Application No. 11160758.6 filed Mar. 31, 2011, and PCT/US2011/066202, filed Dec. 20, 2011; (ii) U.S. Provisional Application Ser. No. 61/434,409, filed Jan. 19, 2011, and PCT/US2011/066216, filed Dec. 20, 2011; (iii) U.S. Provisional Application Ser. No. 61/434,411, filed Jan. 19, 2011, and PCT/US2011/066210, filed Dec. 20, 2011; (iv) U.S. Provisional Application Ser. No. 61/434,413, filed Jan. 19, 2011, and PCT/US2011/066196, filed Dec. 20, 2011; (v) U.S. Provisional Application Ser. No. 61/434,415, filed Jan. 19, 2011, and PCT/US2011/066152, filed Dec. 20, 2011; (vi) U.S. Provisional Application Ser. No. 61/434,417, filed Jan. 19, 2011, and PCT/US2011/066186, filed Dec. 20, 2011; (vii) U.S. Provisional Application Ser. No. 61/434,419, filed Jan. 19, 2011, and PCT/US2011/066206, filed Dec. 20, 2011; (viii) U.S. Provisional Application Ser. No. 61/481,999, filed May 3, 2011, and PCT/US2011/066180, filed Dec. 20, 2011; (ix) U.S. Provisional Application Ser. No. 61/500,854, filed Jun. 24, 2011, and PCT/US2011/066174, filed Dec. 20, 2011; and (x) U.S. Provisional Application Ser. No. 61/504,611, filed Jul. 5, 2011, and PCT/US2011/066165, filed Dec. 20, 2011, the contents of each of which are incorporated by reference in their entirety.

FIELD

The present techniques relate to a method for converting hydrocarbons into conversion products, such as ethylene and propylene, which may be further processed into the other products, such as polyolefins. More particularly, the present techniques relate to an apparatus for implementing the process, which enhances the conversion of hydrocarbons into these products through the use of integrated reactors.

BACKGROUND

The oil, gas and petrochemical industry desires to efficiently obtain hydrocarbons and process the hydrocarbons to produce desired products. Refining processes involve upgrading, converting or separating hydrocarbons (e.g., crude oil) into different streams, such as gases, light naphtha, heavy naphtha, kerosene, diesel, atmospheric gas oil, asphalt, petroleum coke and heavy hydrocarbons or fuel oil. Similarly, natural gas may be converted into industrial fuel gas, liquefied natural gas (LNG), ethane, propane, liquefied petroleum gas (LPG), and natural gas liquids (NGLs). The oil and gas processes are also often integrated with petrochemical systems to convert refinery streams into chemical products, such as ethylene, propylene or polyolefins.

To convert hydrocarbon feeds into petrochemical or basic chemicals, chemical conversion processes may be utilized. These processes typically involve using thermal or chemical reactors or furnaces to produce reactive hydrocarbon products, such as acetylene, ethylene or propylene in different proportions. As an example, steam cracking reactors are commonly utilized to convert the hydrocarbon feed into ethylene and acetylene, which may be further processed into various chemical products. The steam cracking reactors are utilized because they provide feed flexibility by being able to utilize gas (e.g., ethane) and liquid (e.g., naphtha) feeds.

Historically, the oil and gas refineries utilize the higher value distillates from the hydrocarbon feed, which are typically fungible fuels, such as mogas, natural gas and diesel. As a result, the petrochemical refineries utilize the remaining fractions, such as ethane, propane, naphtha and virgin gas oil, in their processes. However, few chemical conversion processes are able to directly employ natural gas or the lower value refinery feeds, such as aromatic gas oils or fuel oils. As such, there is a need for a process that can produce ethylene and acetylene from different feeds, such as advantaged feeds (e.g., natural gas and/or aromatic gas oils, for example).

To process these feeds, high-severity conditions (e.g., more severe operating conditions, such as higher temperatures) are generally involved to produce products having a higher value than the feed. High-severity conditions enable methane cracking and aromatic ring cracking, which do not occur at appreciable rates at typical low-severity conditions (e.g., conventional steam cracking conditions). At high-severity conditions, the primary products of thermal chemical conversion processes are acetylene and ethylene along with hydrogen ($H_2$) and coke, which may vary in proportion depending on the temperatures, pressures, residence times and feed type utilized in the conversion process. Low-severity conditions may be still be used to convert higher hydrogen content refinery byproduct streams. At lower severity conditions, saturates may be converted to ethylene, propylene and butenes and alkyl aromatics may be converted to benzene, toluene and gasoline blend stock. Low-severity reactors operate above 700° C. to enable cracking or conversion to light olefins. Typically, low-severity reactors do not include lower temperature thermal processes, such as cokers or visbreakers, heat soakers, which do not produce substantial light olefins (≥10 wt % light olefin yield). The lower temperature thermal processes may typically operate at temperatures below 700° C. and even more commonly below 600° C. High-severity and low-severity conversion processes are typically based on different pyrolysis reactors, which may include pyrolysis alone or integrated with combustion chemistry. These reactors can be divided into eight different types: low-severity partial combustion, high-severity partial combustion, low-severity indirect combustion, high-severity indirect combustion, low-severity arc process, high-severity arc process, low-severity thermal pyrolysis and high-severity thermal pyrolysis. These pyrolysis reactor types differ in the means of generating and transferring the heat for the pyrolysis and/or in the severity utilized in the operating conditions. For simplicity, these differ types are discussed below as techniques, which include the low-severity and high-severity.

The first technique involves a partial combustion reactor. The partial combustion reactor burns part of the hydrocarbon feed to supply the heat to pyrolyse the remaining portion of the hydrocarbon feed. The partial combustion reactor includes pyrolysis chemistry (e.g., thermochemical decomposition of feed at elevated temperatures in the absence of oxygen) and combustion chemistry (i.e., exothermic chemical reactions between a fuel and an oxidant), with both chemistries occurring at the same time and with the products of both chemistries being an integral part of the reactor product. An example of this process is German Patent No. 875198 and U.S. Pat. Nos. 3,242,223 and 7,208,647. Specifically, U.S. Pat. No. 7,208,647 describes a partial combustion process that utilizes partial oxidation to convert methane into ethylene, while U.S. Pat. No. 3,242,223 describes a partial combustion process that utilizes partial oxidation to convert liquids into ethylene. Due to the nature of this process, however, an air separation plant is typically required and combustion products (e.g., carbon monoxide (CO) and carbon dioxide ($CO_2$)) are significant components of reactor effluent that have to be managed. As a result, the partial combustion process has certain limitations, such as the requirement to remove the high levels of combustion products and associated processing or additional processing equipment.

The second technique involves an indirect combustion reactor. The indirect combustion reactor contacts a combustion product with the feed to be cracked in the reactor. As such, this process involves pyrolysis and combustion chemistry, but typically the combustion chemistry may occur at a different time or location and the pyrolysis chemistry, while occurring in the presence of combustion products, proceeds in a largely non-oxidative environment, resulting in the products of the two chemistries being an integral part of the reactor product. In a process used by Hoechst (High Temperature Pyrolysis) in the 1960s, the thermal energy from a hot combustion product is used to crack a feed in direct contact. Examples of these types of reactors are described in G.B. Patent No. 834419 and German Patent No. 1270537. As another example, the Kureha/UCC process is similar, except that the primary purpose of this process is to make ethylene. In this process, which is described generally in U.S. Pat. No. 3,419,632, the hydrocarbon feed is a crude oil or a distillate having a boiling point less than (<) 1050° C. Further, U.S. Pat. No. 7,208,647 describes an indirect combustion process, which directly contacts the combustion gas with the feed to be cracked. Similar to the discussion for the partial oxidation process, this approach suffers from the same limitations of having to have an air separation plant and manage the combustion products. Accordingly, this type of reactor and associated process also requires an expensive active quench step to stop the pyrolysis chemistry (e.g., water or oil).

The third technique involves an arc reactor, which includes plasma arc reactors and electric arc reactors. This process typically involves only pyrolysis chemistry. Arc reactors are commercially limited and typically operated in a few small plants and described in U.S. Pat. No. 1,860,624. This process involving this type of reactor typically uses a water absorption process for recovery of acetylene, which was initially developed in the 1940s. The electric arc process utilizes electric power to heat a feed. As an example, U.S. Pat. No. 7,119,240 describes an electric arc reactor and process. The drawback of the arc process is the high cost of utilities, such as electricity, required to generate the "arc" or plasma. As a result, this process is limited to small units integrated with supplies of "cheap" electricity, such as a hydroelectric plants or nuclear facilities.

The fourth technique involves a thermal pyrolysis reactor. Thermal pyrolysis reactors involve heating a solid material (e.g., by combustion) and using the heated solid material to provide heat to crack the pyrolysis feed (e.g., via pyrolysis chemistry alone). In the thermal pyrolysis processes, the combustion products are typically maintained separate from the pyrolysis hydrocarbon products or effluent. This pyrolysis technique involves various different types of reactors, such as a furnace (e.g., as used in steam cracking), a regenerative reactor (e.g., as used in the Wulff process) and others. For instance, thermal cracking is generally described in various references, such as U.S. Pat. Nos. 7,138,047 and 7,119,240. U.S. Pat. No. 7,119,240 describes an exemplary process for the conversion of natural gas into ethylene. In this process, natural gas is cracked in a furnace, actively quenched, and processed in a reactor to produce ethylene. As another example, U.S. Pat. No. 7,138,047 describes another steam cracking process that mixes a hydrocarbon feed with a dilution steam, flashing the mixture, and vaporizing a portion of the mixture in a pyrolysis reactor. In the process, the pyrolysis feed is passed through tubes in the radiant section of a pyrolysis reactor to crack the pyrolysis feed without contaminating it with combustion products. However, due to the nature of a tubular (metal) furnace, steam cracking is limited to effective cracking temperatures of below 1000° C. and residence times of≥100 milliseconds (ms), which do not allow conversion of either methane or aromatics, thereby limiting the feedstock selection. In addition, energy or furnace heat not used in cracking is partially lost in the furnace flue gas or in the quench, as products are quickly cooled to stop undesired reactions.

The "Wulff" reactor, as described in the IHS, SRI Consulting's Process Economics Program "Acetylene" Report Number 16 (1966) and 16A (1982) along with U.S. Pat. Nos. 2,319,679; 2,678,339; 2,692,819; 3,024,094, and 3,093,697, uses a reverse-flow pyrolysis reactor, which is typically operated at temperatures of<1400° C., to produce olefins and alkynes, such as acetylene. The pyrolysis feed is heated by refractories which have previously been heated by combustion reactions. The pyrolysis feed is cracked, and then cooled outside of the reactor. The relatively slow quenching is a characteristic of the Wulff process that leads to coke and soot formation from using inefficient indirect heat transfer (e.g., from checker brick). Coke formation in the reactor provides fuel during the combustion cycle and excess coke or soot may be alleviated by using a light feed, i.e., a hydrocarbon containing a high proportion of hydrogen. However, because the indirect heat transfer limits the rate of heat input in the Wulff process, certain pyrolysis feeds, such as methane, may not be economically processed, which limits the feed flexibility for this process. As a result, these reactors typically have limitations, such as poor heat transfer and greater soot generation resulting in poorer selectivity to desired products.

While the prior art describes using different pyrolysis reactors, these reactors described include various limitations, which reduce the efficiency of the process. For example, steam cracking is efficient in converting naphtha, but not efficient in converting methane. Likewise, certain high temperature pyrolysis techniques are more effective in converting methane, but too expensive to effectively convert naphtha. Accordingly, it is desirable to provide a process that converts hydrocarbon feeds into olefins, such as ethylene, in an enhanced manner with different reactors types to efficiently convert a broader range of feed molecules. In particular, it is desirable to provide a configuration that provides flexibility in the hydrocarbon feed utilized for olefin recovery. Accordingly, various combinations of different pyrolysis reactors are envisioned, where each type of pyrolysis reactor may efficiently crack a preferred portion of a hydrocarbon feed, which are described further below. These pyrolysis reactors may be coupled together with each of the reactors being associated with a different portion of the hydrocarbon feed.

SUMMARY

In one aspect, one or more embodiments of the present techniques provide a method for enhancing the conversion of hydrocarbon feeds into conversion products, such as ethylene and propylene. In particular, the present techniques utilize a high-severity reactor integrated with another reactor type to convert hydrocarbons to other petrochemical products in an enhanced manner.

In an embodiment, the invention relates to a hydrocarbon conversion method comprising:

exposing a first pyrolysis feed in a first pyrolysis reactor to a peak pyrolysis gas temperature≥1400.0° C. to produce a first reactor product comprising ethylene and acetylene, wherein the first pyrolysis feed has (i) a hydrogen content in the range of 6.0 wt. % to 25.0 wt % based on the weight of hydrocarbon in the pyrolysis feed and/or (ii) a non-combustible, non-volatiles content<2.0 ppm based on the weight of the first pyrolysis feed;

exposing a second pyrolysis feed to pyrolysis conditions in a second pyrolysis reactor produce a second reactor product comprising ethylene and acetylene, wherein the first and second pyrolysis reactors are of different type and (i) the second pyrolysis feed has (i) a hydrogen content in the range of 6.0 wt % to 20.0 wt % based on based on the weight of hydrocarbon in the pyrolysis feed and/or (ii) a non-combustible, non-volatiles content≥2.0 ppm based on the weight of the second pyrolysis feed; and combining at least a portion of the first reactor product and at least a portion of the second reactor product to form a combined reactor product; wherein the first and second pyrolysis feeds comprise hydrocarbons, the hydrocarbons being derived from a hydrocarbon feed having a hydrogen content in the range of≤24.0 wt %.

In another embodiment, this invention relates to an apparatus for processing hydrocarbons comprising:

a first pyrolysis reactor configured to expose a first pyrolysis feed to high-severity operating conditions to produce a first reactor product comprising ethylene and acetylene, wherein the first pyrolysis feed has (i) a hydrogen content in the range of 6.0 wt % to 25.0 wt % based on the weight of hydrocarbon in the pyrolysis feed and/or (ii) a non-combustible, non-volatiles content<2.0 ppm based on the weight of the first pyrolysis feed;

a second pyrolysis reactor configured to crack a second pyrolysis feed to produce a second reactor product comprising ethylene and acetylene, wherein the first and second pyrolysis reactors are of different type and the second pyrolysis feed has (i) a hydrogen content in the range of 6.0 wt % to 20.0 wt % based on based on the weight of hydrocarbon in the pyrolysis feed and/or (ii) a non-combustible, non-volatiles content≥2.0 ppm based on the weight of the second pyrolysis feed; and a combining unit in fluid communication with the first pyrolysis reactor and the second pyrolysis reactor and configured to combined at least a portion of the first reactor product and at least a portion of the second reactor product into a combined reactor product.

Further in one or more embodiments, a method for processing hydrocarbons is described. The method comprising passing a first pyrolysis feed to a first pyrolysis reactor; exposing at least a portion of the first pyrolysis feed in the first pyrolysis reactor at high-severity operating conditions that include peak pyrolysis gas temperatures≥1400° C. to produce a first reactor product; passing a second pyrolysis feed to a second pyrolysis reactor, wherein the first pyrolysis reactor and the second pyrolysis reactor are different pyrolysis reactor types; cracking at least a portion of the second pyrolysis feed in the second pyrolysis reactor to produce a second reactor product; and combining at least a portion of the first reactor product and at least a portion of the second reactor product to form a combined reactor product, wherein the first reactor product and the second reactor product each comprise ethylene and acetylene. The hydrocarbons in the combined reactor product may predominately include ethylene and acetylene ($C_2$ unsaturates ($C_2U$) in the reactor product, each of the reactor products may include $C_2U$ at a level greater than or equal to (≥) 1 wt %, ≥5 wt % or even≥10 wt % in the reactor product.

Moreover, in one or more embodiments, an apparatus for processing hydrocarbons is described that includes a first pyrolysis reactor, a second pyrolysis reactor and combining unit. The first pyrolysis reactor is configured to expose a first pyrolysis feed to high-severity operating conditions to produce a first reactor product; while the second pyrolysis reactor is configured to crack a second pyrolysis feed to produce a second reactor product, wherein the second pyrolysis reactor and the first pyrolysis reactor are different reactor types. The combining unit is in fluid communication with the first pyrolysis reactor and the second pyrolysis reactor and is configured to combine at least a portion of the first reactor product and at least a portion of the second reactor product into a combined reactor product.

Further, other units may be utilized with this process. For instance, a separation unit may be in fluid communication with the first pyrolysis reactor and configured to separate a bottoms product comprising tars and/or solids from the first reactor product from the first pyrolysis reactor. A converter may be in fluid communication with the combining unit and may be configured to convert at least a portion of the remaining reactor product into a conversion product. A polymerization unit may be in fluid communication with the converter and may be configured to convert at least a portion of the conversion product into polyethylene. Other separation units, such as a hydrogen separation unit, may be utilized to separate other products from the remaining reactor product as it is processed into a specific product.

In one or more embodiments, method or apparatus may be operated in a manner to manage the process in an enhanced manner. For instance, the first pyrolysis reactor may be a thermal pyrolysis reactor operated at operating conditions comprising a $C_3^+$ to acetylene weight ratio less than or equal to (≤)_0.5, ≤0.45, and/or≤0.4. Further, the peak pyrolysis gas temperature of the first pyrolysis reactor may be equal to or above 1540° C., between 1450° C. and 1900° C., and/or between 1540° C. and 1800° C. The residence time for the at least a portion of the first pyrolysis feed within the first pyrolysis reactor may be between 0.5 second and 0.001 second. The method may involve pressures≥3 pounds per square inch gauge (psig) (21 kiloPascal gauge (kPag)), 15 psig (103 kPag), ≥36 psig (248 kPag), ≥44 psig (303 kPag) or≥103 psig (710 kPag), but may be≤300 psig (2068 kPag), ≤163 psig (1124 kPag), or≤150 psig (1034 kPag).

In other embodiments, the method and/or apparatus may be utilized to efficiently process a hydrocarbon feed. For instance, the method may involve separating a hydrocarbon feed, such as methane, crude oil or crude oil components, into the first pyrolysis feed and the second pyrolysis feed. These feeds may have similar compositions or may have different compositions (e.g., divided into different fractions that are processed more efficiently in different reactors). The different reactors may include the first pyrolysis reactor as one of a partial oxidation reactor, an arc reactor, thermal pyrolysis reactor, while the second pyrolysis reactor may be a reactor that operates at low-severity operating conditions to produce the second reactor product, such as a steam cracking reactor.

Further still, in other embodiments, the first pyrolysis reactor may be a regenerative reverse flow thermal pyrolysis reactor. This reactor may comprise a reactor body, wherein the reactor body forms a reaction region within the reactor body; a packing material disposed at least partially within the reaction region; and one or more poppet valve assemblies coupled to the reactor body and in flow communication with the reaction region and controlling fluid flow of the at least a portion of the first pyrolysis feed between a location external to the reactor body and within the reaction region. In the reactor, different combustion feeds may each be separately heated within the first pyrolysis reactor prior to exothermically reacting in the region.

Figure 1A:
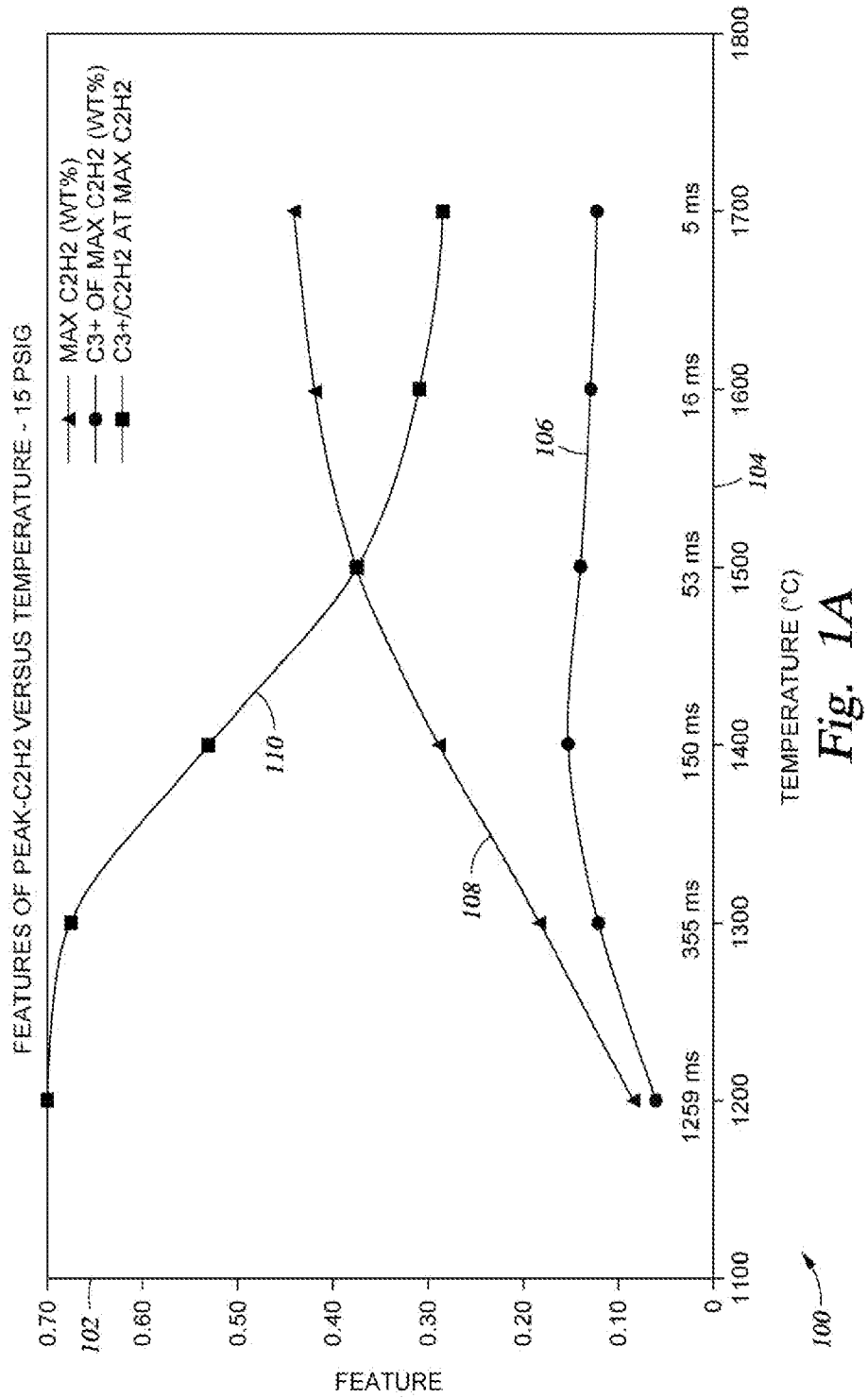
FIGS. 1A and 1F are diagrams of simulation results representing different ratios of reactor products produced at different temperatures and/or different pressures.

Although the invention is described in terms of a pyrolysis process for producing acetylene and ethylene, the invention is not limited thereto. In other words, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention, as defined by the appended claims

DETAILED DESCRIPTION OF THE EMBODIMENTS

In contrast to conventional techniques, the present techniques provide an enhanced process for conversion of feed containing hydrocarbons into olefins, such as acetylene and ethylene and optionally polyolefins. The present techniques utilize two different types of pyrolysis reactors with one being configured to expose a first pyrolysis feed to higher temperatures than conventional steam cracking and the other being configured to crack a second pyrolysis feed. These higher temperatures are utilized to crack feeds that are normally unreactive or react to low value products (e.g., degraded products) at lower temperatures. As a specific example, at temperatures≥1200.0° C., methane and aromatic components are partially cracked to yield $C_2$ unsaturates ($C_2U$) compounds, typically acetylenes and ethylene. At temperatures≥1400.0° C. or preferably≥1540.0° C., aromatics and methane may be cracked at high conversion levels, with selectivity levels≥50 wt % to light gas products. At atmospheric pressure, higher temperature also provides selectivity to enhance the yield of $C_2U$ (e.g., yield of ethylene and acetylene). In addition, the ethylene to acetylene weight ratio (E/A) can be≤0.10 or as low as 0.02 (at residence times≤0.1 ms) at atmospheric pressure and high severity.

The second pyrolysis reactor may yield other portions of reactor products (e.g., the product species may be similar, but the compositions or yields may be in differing amounts). For example, if the second pyrolysis reactor is operated at low-severity conditions, it may be used to crack refinery byproduct streams that typically have a higher concentration of saturated hydrocarbons that may crack at lower temperatures. These streams may be converted at temperature below 1200.0° C. to ethylene and/or propylene and do not require the higher temperatures to upgrade the conversion process. As a result, the conversion process is more efficient.

As a result, the present techniques provide a more efficient process to recover olefins by integrating different reactor types. For instance, present techniques provide flexibility in type of hydrocarbon feed utilized in the process. That is, any hydrocarbon feed provided may be separated into different streams for the different pyrolysis reactors, which operate one of the reactors as a high-severity reactor. In this manner, a broader range of hydrocarbon feeds may be utilized with the second pyrolysis reactor efficiently processing a specific portion of the hydrocarbon feed and the first pyrolysis reactor efficiently processing another portion of the hydrocarbon feed. Further, as the product species are similar, the recovery stage for these reactors may be integrated to efficiently process the reactor products from the respective reactors. To further explain the high-severity pyrolysis reactor and its associated products, various simulation results representing different ratios of reactor products produced at different temperatures and/or different pressures are provided. These simulations utilize certain feeds, such as methane, for simplicity, but the invention is not limited thereto. The benefits of this configuration provide a more efficient process to recover olefins by integrating different pyrolysis reactor types. For instance, in this configuration, one of the enhancements is the flexibility in the hydrocarbon feed utilized for olefin recovery. That is, any hydrocarbon feed provided may be separated into different streams for the first pyrolysis reactor and the second pyrolysis reactor. For instance, the first pyrolysis feed may be derived from a broader range of hydrocarbon feeds with lower hydrogen contents and advantaged feeds (e.g., heavy aromatic to methane), while the second pyrolysis feed may be derived from specific feeds which may not require the high-severity operating conditions, e.g., saturates. These feeds, which do not typically react in at low-severity condition or react to lower value products, react in the process to provide $C_2U$. High-severity, as provided in the present process, converts at high levels aromatic containing and/or methane containing feeds to valuable $C_2$ products. Various combinations of different pyrolysis reactors may be envisioned, where each type of reactor may efficiently crack a preferred portion of a hydrocarbon feed. As such, a group of reactors may be coupled together with each associated with different portions of the hydrocarbon feeds, which typically foul or are unreactive in other process.

At any elevated temperature, hydrocarbon pyrolysis or hydropyrolysis produces acetylene at an intermediate residence time. As time continues, the hydrocarbons react further towards condensed species and eventually carbon (e.g., produce more coke). Thus, there is a maximum amount of acetylene, which is achieved at a specific residence time, and which is the optimum acetylene yield for a given temperature. The temperature and residence time of this maximum acetylene yield can be used to characterize thermal pyrolysis reactor performance at that temperature, in terms of the yield of $C_3^+$ in relationship to the yield of acetylene. The yield of $C_3^+$, as used herein, includes all $C_3^+$ products of the pyrolysis feed, whether those products emerge from the reactor or remain within the reactor as coke. $C_3^+$ includes, for example, products such as methyl acetylene, benzene and tar, and is specifically defined as including carbonaceous byproducts, such as coke. The maximum acetylene yield, the corresponding $C_3^+$ yield and the acetylene to $C_3^+$ weight ratio are described further in relation to temperature and residence time in FIGS. 1A and 1B and Table 1.

Figure 1B:
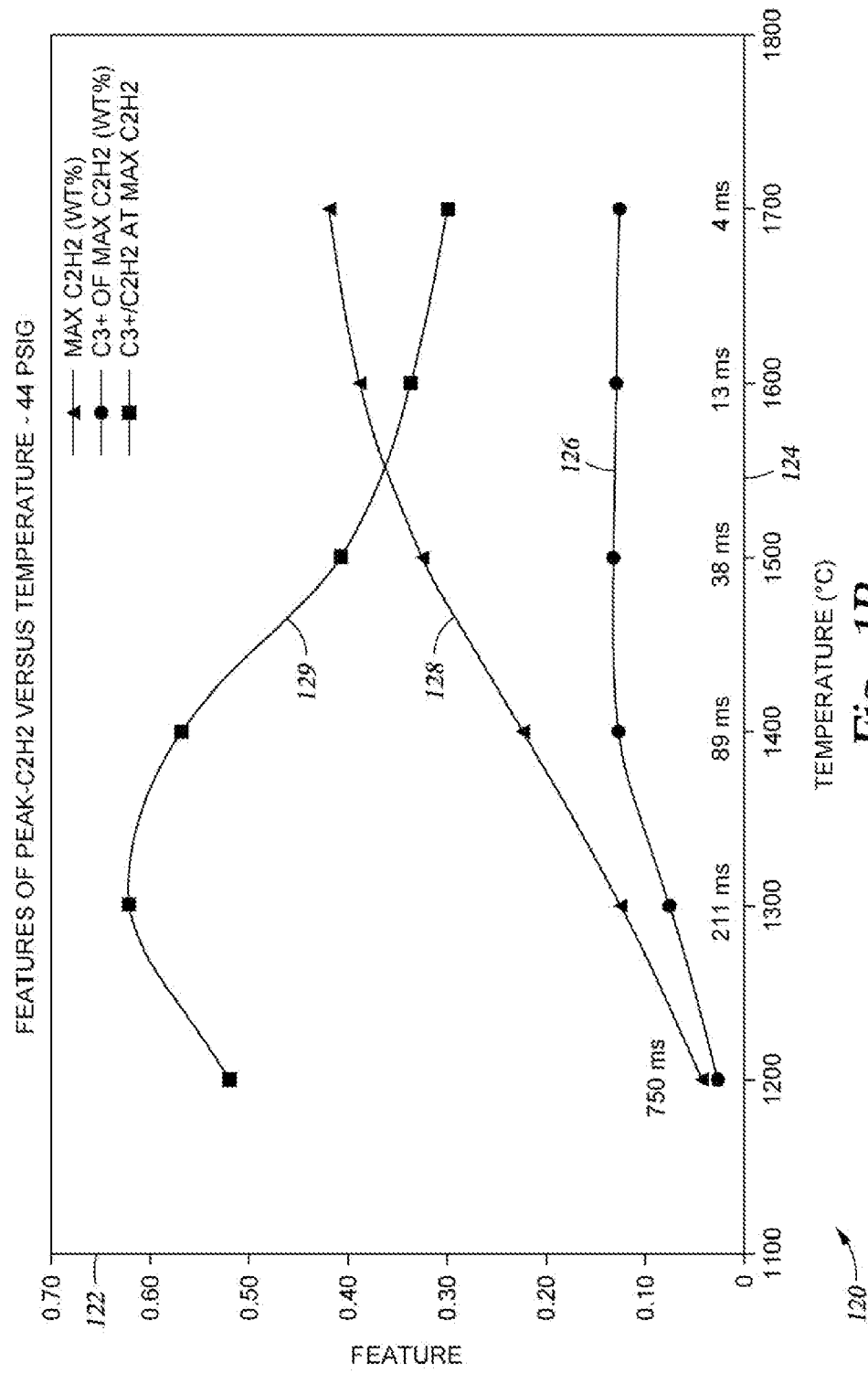

FIGS. 1A and 1B illustrate the simulation results for different ratios of reactor products produced at different temperatures from a methane feed. The consequences of operating at various temperatures are provided for comparison of the product yields achievable at the residence time associated with the maximum acetylene yield for that temperature. Pyrolysis, in this example, is carried out under isothermal conditions, with 2:1 molar diluent of hydrogen in a methane feed, and at 14.7 psig (101 kPag) pressure for diagram 100 and at 44 psig (303 kPag) pressure for diagram 120. All hydrocarbon products larger than $C_2$ are considered as $C_3^+$ in this example and the product is the reaction product yield from the converted pyrolysis feed. In diagram 100, certain values for maximum acetylene yield 108 in weight percent (wt %) of the product, and corresponding $C_3^+$ yield 106 in wt % of the product, and $C_3^+$ to acetylene weight ratio 110 of the product are shown along the Y-axis 102 for various temperatures (in ° C.) along the X-axis 104. The $C_3^+$ to acetylene weight ratio 110 has a peak between the temperatures of 1200° C. and 1400° C., which decreases at a slower rate as temperature increases from 1500° C. or 1540° C. Similarly, in diagram 120, certain values for a maximum acetylene yield 128 in wt % of the product, and corresponding $C_3^+$ yield 126 in wt % of the product, and $C_3^+$ to acetylene weight ratio 129 of the product are shown along the Y-axis 122 for various temperatures (in ° C.) along the X-axis 124. The $C_3^+$ to acetylene weight ratio 110 again has a peak within the range of 1300° C. to 1400° C., which decreases at a slower rate from 1500° C. or 1540° C. as the temperature increases. As such, operating conditions of the thermal pyrolysis reactor may be adjusted to enhance the acetylene yield for a pyrolysis feed.

This aspect is further described in Table 1, which includes simulation results for different ratios of reactor products produced at different temperatures from methane. The consequences of operating at various temperatures are provided for comparison of the product yields achievable at the residence time associated with the maximum acetylene yield for that temperature. Pyrolysis, in this example, is carried out under isothermal conditions, with 2:1 molar diluent of hydrogen (as $H_2$) in a methane feed, and at 14.7 psig (101 kPag) reactor pressure. Table 1 lists the results, such as composition of the pyrolysis product (weight percent of total pyrolysis product), for operations at temperatures between 1200° C. and 2200° C.:

As shown in this table, the maximum acetylene yield increases rapidly with temperature until 1500° C. Above this temperature, the maximum acetylene yield increases at a slower rate. Further, the residence time required to achieve this conversion decreases with increasing temperature. For instance, at 1200° C., residence times over 1 second are needed, and acetylene comprises only about 8.6 wt % of the products, while at 1700° C., residence times of about 5 milliseconds are needed and acetylene comprises 44.0 wt % of the products. Residence time has a large impact on reactor volume (proportional to the reciprocal of residence time). As a result, a given unit of reactor may process more pyrolysis feed when the reactor temperature is high and residence time is low. However, the very short residence times that achieve optimal acetylene yields at very high temperatures may place demands on certain reactor components that may exceed practicality. For example, where the pyrolysis feed is being flowed through the hot region of the pyrolysis reactor, the required gas velocity is roughly equal to the length of the hot region divided by the desired residence time. Gas velocities in flow channels and valve orifices are preferred to be less than the velocity of sound, which may result in reactor lengths that are not practical. In addition, because thermal pyrolysis involves the transfer of heat through a solid intermediary from a combustion step to a pyrolysis step, extremely short residence times may impose a heat transfer rate requirement (heat of reaction divided by reaction time) that may not be practical. As such, the design and operating conditions of the reactor may limit the maximum temperature that may be utilized to crack the pyrolysis feed.

Even though maximum acetylene ($C_2H_2$) yield increases for methane with increasing temperature, the $C_3^+$ yield is greatest for intermediate temperatures, such as 1400° C. Dividing $C_3^+$ yield by acetylene yield gives a selectivity parameter ($C_3^+/C_2H_2$) that indicates how much $C_3^+$, which is related to coke production, has to be managed per unit of acetylene produced. This selectivity parameter remains very high (e.g., ≥0.5) for temperatures below 1500° C., and drops into a lower section (e.g., ≤0.45 or ≤0.4) for temperatures at or above 1500° C.

For feeds containing high levels of aromatics or methane, temperatures below 1500° C. are not as effective for production of acetylene because of the high $C_3^+$ yields, the low acetylene yields, and the relatively long residence times (e.g., large reactor volumes) needed for processing. Conversely, considering the broad range of temperature cited for

TABLE 1

| Temperature (° C.) | 1200 | 1300 | 1400 | 1500 | 1540 | 1600 | 1650 | 1700 | 2200 |
|---|---|---|---|---|---|---|---|---|---|
| Max $C_2H_2$ (wt % of product) | 8.6% | 18.1% | 28.8% | 37.5% | 39.6% | 41.8% | 43.0% | 44.0% | 49.4% |
| Time of max $C_2H_2$ (sec) | 1.259 | 0.355 | 0.150 | 0.053 | 0.035 | 0.016 | 0.009 | 0.005 | 0.00006 |
| $C_3^+$ (wt % of product) | 6.0% | 12.2% | 15.3% | 14.0% | 13.7% | 12.9% | 12.6% | 12.3% | 12.9% |
| $C_3^+/C_2H_2$ | 0.699 | 0.673 | 0.530 | 0.372 | 0.346 | 0.308 | 0.293 | 0.281 | 0.261 |
| $C_2H_2$/unit reactor volume (relative units) | 0.068 | 0.510 | 1.928 | 7.066 | 11.31 | 26.38 | 47.8 | 92.98 | 8233 |
| $CH_4$ conversion | 29.9% | 53.4% | 73.3% | 83.1% | 84.6% | 86.9% | 88.8% | 88.7% | 96.9% |
| $H_2$ (wt % of product) | 24.2% | 27.9% | 31.2% | 32.9% | 33.2% | 33.6% | 34.0% | 33.9% | 34.8% |
| Surplus $H_2$ (wt % of prod.) | 3.5% | 6.5% | 8.9% | 10.0% | 10.1% | 10.3% | 10.6% | 10.4% | 11.0% | methane pyrolysis, there is an advantage to operating at temperatures above 1500° C., in terms of $C_2U$ yield and $C_2$ selectivity.

The high severity pyrolysis is also substantially impacted by ratio of hydrogen ($H_2$) gas to feed hydrocarbon carbon (C), as shown in Table 2, below. Pyrolysis, in this example, is carried out under isothermal conditions, for a feed containing methane gas and optionally hydrogen gas, at a temperature of 1550° C. and at 14.7 psig (101 kPag) reactor pressure. Residence time, in each case, is chosen to give 70 wt % conversion of the methane feed. Table 2 lists the results, such as composition of the pyrolysis product (weight percent of total pyrolysis product) for operations at $H_2/C$ levels between 0 and 5:

TABLE 2

| | $H_2/CH_4$ (molar ratio) | | | | | |
|---|---|---|---|---|---|---|
| | 0 | 1 | 2 | 3 | 4 | 5 |
| Residence time, sec | 0.004 | 0.007 | 0.011 | 0.014 | 0.018 | 0.021 |
| $CH_4$ Conversion: | 70.0% | 70.0% | 70.0% | 70.0% | 70.0% | 70.0% |
| $C_2U$, wt % | 28.2% | 34.7% | 36.0% | 35.1% | 33.4% | 31.6% |
| $C_3+$, wt % | 28.2% | 15.6% | 9.3% | 6.1% | 4.4% | 3.3% |
| Hydrogen ($H_2$), wt % | 13.5% | 23.1% | 30.7% | 37.0% | 42.2% | 46.7% |
| $C_3+/C_2U$ | 1.000 | 0.449 | 0.259 | 0.175 | 0.131 | 0.104 |
| relative $C_2$ productivity: | 509 | 280 | 168 | 111 | 78 | 57 |

As shown in Table 2, increasing hydrogen ($H_2$) diluent results has a small impact on $C_2U$ (e.g., acetylene and ethylene) yield, however increasing hydrogen diluent results in a substantial decrease $C_3^+$ yield and corresponding decrease in $C_3^+/C_2U$ weight ratio. Low hydrogen diluent levels may result in an unacceptably high level of $C_3^+$ yield and corresponding decrease in $C_3^+/C_2U$ weight ratio. High hydrogen diluent levels have a deleterious impact on reactor productivity because (a) the dilution reduces kinetic rates resulting in longer residence times (larger reactors) to achieve the same productivity, and (b) because $H_2$ dilution reduced the amount of hydrocarbon (and hence hydrocarbon products) that are carried in each volume of gas. These effects are reflected in the relative $C_2$ productivity entry in Table 2, which shows in relative terms the impact of hydrogen dilution on amount of $C_2$'s that are produced in a unit of reactor volume. High hydrogen dilution may also result in debits in process equipment outside of the pyrolysis reactor due to the larger volumes of gases that have to be managed per unit of pyrolysis product produced. Thus, there is an optimum amount of hydrogen diluent at moderate levels between 0 and 5. Accordingly, the present techniques, by means of high temperature pyrolysis, achieve at low $H_2/C$ molar ratio, a level of $C_3^+/C_2U$ that would otherwise require operating at high (and less economical) levels of $H_2/C$.

As shown in Table 3 below, conditions and yields for the pyrolysis of hydrogen deficient feeds may be different than those for the pyrolysis of hydrogen rich feeds shown in Table 1. A hydrogen deficient feed, in this example toluene having 8.7 wt % hydrogen content, is pyrolyzed at 1445° C., 4 psig (28 kPag) pressure, for a residence time of 0.08 seconds with a hydrogen diluent at a level of 28 moles $H_2$ gas per mole of hydrocarbon carbon. In this toluene conversion case, a high $H_2/C$ molar ratio is employed to compensate for a low (1445° C.) pyrolysis temperature, while still achieving acceptable $C_3+/C_2U$ performance, thus illustrating features of toluene cracking. As indicated above, a more preferred operation would pyrolyze the toluene at higher temperature and lower $H_2/C$ molar ratio.

TABLE 3

| Pyrolysis of Toluene (8.7 wt % H) | | Products: wt % of toluene feed | | wt/wt | |
|---|---|---|---|---|---|
| Pressure (psig) | 4 | Methane | 26% | $C_3^+/C_2H_2$ | 0.351 |
| Temp (C.) | 1445 | Ethylene | 12% | $C_3^+/C_2U$ | 0.283 |
| Residence time, ms | 80 | Acetylene | 49% | E/A | 0.238 |
| $H_2/C$ | 28 | $C_3^+$ | 17% | | |
| | | $H_2$ | −5% | | |

As shown in Table 3, the pyrolysis results in a high conversion to acetylene (49 wt %) and ethylene (12 wt %), but also yields 17 wt % $C_3^+$ materials (mostly coke and tar). In contrast to the pyrolysis of hydrogen rich feed (Table 1), the hydropyrolysis of hydrogen deficient feed results in a consumption of hydrogen (from the $H_2$ diluent), and the production of methane (26 wt % of feed toluene) as a product. Accordingly, it is advantageous to recycle the excess hydrogen ($H_2$) and methane gas that is produced from pyrolysis to be combined into the pyrolysis feed.

While the high-severity temperatures may be preferred if the objective of the process is to produce acetylene, variations in pressure along with the high-severity temperatures may enhance the distribution of $C_2$ compounds (e.g., yield of ethane, ethylene and acetylene) and the distribution of other light hydrocarbons (e.g., propylene, propyne, etc.). Accordingly, these pressure variations may be utilized if ethylene and/or other olefins are the preferred product. As an example, steam cracking typically utilizes lower temperature to convert ethane to ethylene and trace levels of acetylene. At atmospheric pressure, lower temperatures result in higher ethylene to acetylene (E/A) weight ratios. However, lower temperatures also provide poor conversions for methane and aromatics, which as noted above, is inefficient. At high-severity conditions (e.g., temperatures≥1400° C. or preferably ≥1540° C., for example) aromatics and methane may be cracked at high conversion levels, with selectivity levels≥50 wt % to light gas products. Also shown in Table 1, at temperatures ≥1400° C., selectivity levels≥50 wt % to light gas products are achievable. For example, at 1540° C., products of methane make up 67.8 wt % of the pyrolysis product, including $H_2$, $C_2$'s, and $C_3^+$. Thus, the selectivity to $C_3^+$ is 20 wt % (13.7 wt %/67.8 wt %), and the selectivity to lighter gas products is 80 wt %. Further, by varying the pressure from atmospheric to elevated pressures (e.g., up to 300 psig), ethylene to acetylene (E/A) weight ratios≥0.1, ≥0.2, ≥0.4 or even≥0.5 may be achieved. The variations of pressure at high-severity operating conditions are described below in Tables 4 and 5 and FIGS. 1C to 1F.

Table 4 includes simulation results for different ratios of reactor products produced at different pressures for different temperatures from a methane feed. Pyrolysis, in this example, is carried out under isothermal conditions at 1500° C. and at 1650° C., with 2:1 molar diluent of hydrogen in a methane feed, and at 15 psig (103 kPag) reactor pressure to 162 psig (1117 kPag) reactor pressure. All products larger than $C_2$ are considered as $C_3^+$ in this example and the product is the reaction product yield from the converted pyrolysis feed.

TABLE 4

70% Isothermal Conversion Data

| Temp (° C.) | P (psig) | time (sec) | Conv. | Products (weight percent) | | | | | | $C_3^+/C_2U$ | E/A |
|---|---|---|---|---|---|---|---|---|---|---|---|
| | | | | $H_2$ | $CH_4$ | $C_2H_2$ | $C_2H_4$ | $C_3^+$ | $C_2U$ | | |
| 1500 | 15  | 0.025  | 72% | 31.1 | 22.0 | 34.2 | 2.0 | 10.7 | 36.0 | 0.30 | 0.06 |
| 1500 | 36  | 0.025  | 73% | 31.1 | 21.7 | 32.7 | 3.1 | 11.3 | 36.0 | 0.32 | 0.10 |
| 1500 | 44  | 0.025  | 72% | 31.0 | 22.1 | 31.9 | 3.5 | 11.5 | 35.0 | 0.33 | 0.11 |
| 1500 | 59  | 0.025  | 71% | 30.7 | 23.3 | 30.3 | 4.1 | 11.6 | 34.0 | 0.34 | 0.14 |
| 1500 | 74  | 0.025  | 69% | 30.4 | 24.7 | 28.6 | 4.6 | 11.7 | 33.0 | 0.35 | 0.16 |
| 1500 | 103 | 0.025  | 65% | 29.7 | 27.9 | 25.4 | 5.4 | 11.5 | 31.0 | 0.37 | 0.21 |
| 1500 | 162 | 0.025  | 57% | 28.4 | 34.3 | 20.3 | 6.3 | 10.8 | 27.0 | 0.41 | 0.31 |
| 1650 | 15  | 0.0025 | 68% | 30.4 | 25.4 | 35.0 | 1.0 | 8.2 | 36.0 | 0.23 | 0.03 |
| 1650 | 36  | 0.0025 | 71% | 30.8 | 23.6 | 35.6 | 1.5 | 8.5 | 37.0 | 0.23 | 0.04 |
| 1650 | 44  | 0.0025 | 71% | 30.8 | 23.3 | 35.6 | 1.7 | 8.6 | 37.0 | 0.23 | 0.05 |
| 1650 | 59  | 0.0025 | 71% | 30.9 | 22.9 | 35.4 | 2.0 | 8.7 | 37.0 | 0.23 | 0.06 |
| 1650 | 74  | 0.0025 | 71% | 30.9 | 22.8 | 35.2 | 2.3 | 8.8 | 37.0 | 0.24 | 0.07 |
| 1650 | 103 | 0.0025 | 71% | 30.8 | 22.9 | 34.4 | 3.0 | 8.9 | 37.0 | 0.24 | 0.09 |
| 1650 | 162 | 0.0025 | 70% | 30.5 | 24.0 | 32.5 | 4.1 | 9.0 | 37.0 | 0.25 | 0.13 |

As shown in Table 4, as pressure increases from 15 psig (103 kPag) to 162 psig (1117 kPag), CU yields in wt % of the product are roughly constant at about 33 wt % (+/−10 wt %) for 25 millisecond (ms) residence time at 1500° C. However, the E/A weight ratios improve over this increase in pressure. At 1650° C., the CU yields in wt % of the product are again roughly constant at about 37 wt % (+/−10 wt %) for 2.5 ms, while the E/A weight ratio increases fourfold. Accordingly, the higher pressures tend to lead to higher E/A weight ratios. Further, the $C_3^+$ yields in wt % of the product at these different temperatures and pressures also remain relatively constant at 12% for 1500° C. and 9% for 1650° C. As a result, the $C_3^+$ to $C_2U$ weight ratio ($C_3^+/C_2U$) increases at slow rate with pressure at the lower temperature, while the higher temperatures provide a roughly constant $C_3^+$ to $C_2$ unsaturate weight ratio.

From this table, the yield of CU (e.g., acetylene and ethylene) may be optimized for certain operating conditions. That is, a specific pressure, temperature and residence time may be utilized to optimize the distribution of $C_2U$ yield. These operating conditions may be characterized by the $C_3^+$ to $C_2U$ weight ratio along with an E/A weight ratio, which may be further explained in view of the FIGS. 1C and 1D.

Figure 1C:
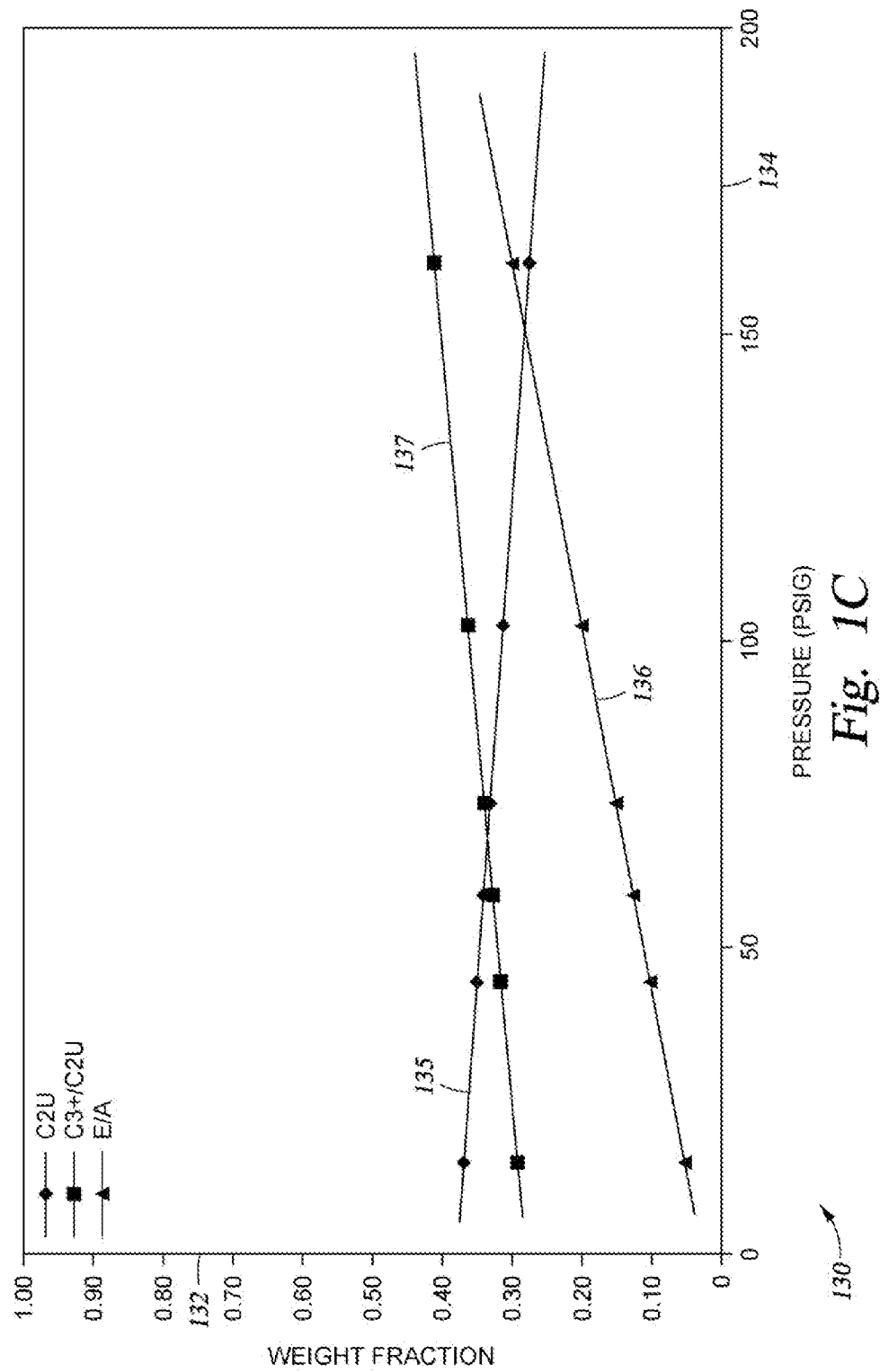
Figure 1D:
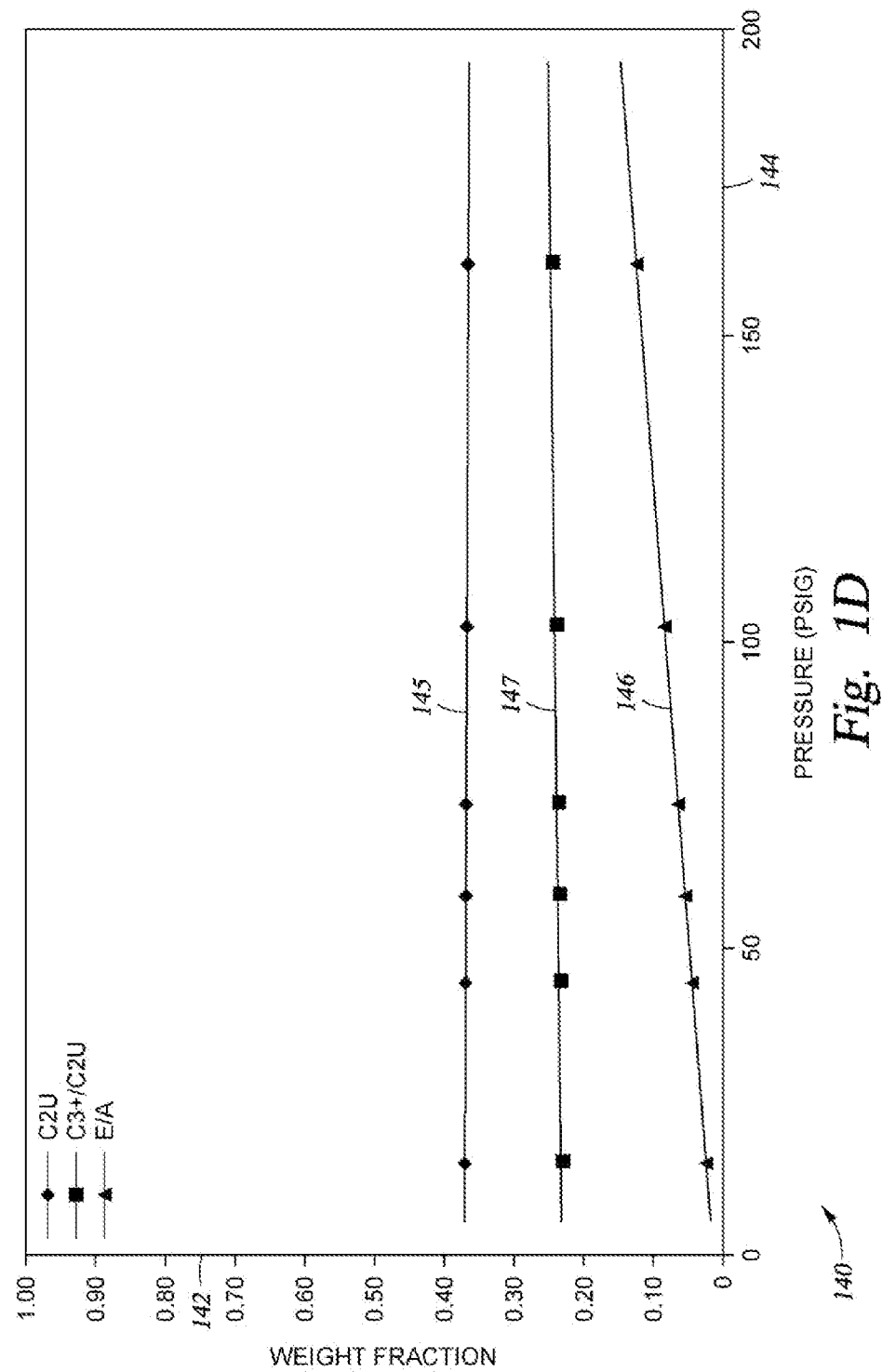

FIGS. 1C and 1D illustrate the simulation results for different ratios of reactor products produced at different pressures for certain temperatures from methane. The results of operating at the various pressures are provided for comparison of the product yields achievable at the residence times associated with the $C_2U$ yield and an E/A weight ratio for that pressure. Pyrolysis, in this example, is carried out under isothermal conditions, with 2:1 molar diluent of hydrogen in a methane feed, and at 1500° C. for diagram 130 and at 1650° C. for diagram 140. All products larger than $C_2$ are considered as $C_3^+$ in this example and the product is the reaction product yield from the converted pyrolysis feed. In diagram 130, certain values for a $C_2U$ yield 135 in wt % of the product, ethylene to acetylene weight ratio 136, and $C_3^+$ to $C_2U$ weight ratio 137 are shown in weight fraction (or weight ratio) along the Y-axis 132 for various pressures (in psig) along the X-axis 134. The ethylene to acetylene weight ratio 136 and $C_3^+$ to $C_2U$ weight ratio 137 increases with increasing pressure, while the $C_2U$ yield 135 decreases slightly with increasing pressure. Similarly, in diagram 140, certain values for a $C_2U$ yield 145 in wt % of the product, ethylene to acetylene weight ratio 146, and $C_3^+$ to $C_2U$ weight ratio 147 are shown in weight fraction (or weight ratio) along the Y-axis 142 for various pressures (in psig) along the X-axis 144. The ethylene to acetylene weight ratio 146 increases with increasing pressure, while the $C_2U$ yield 145 and $C_3^+$ to $C_2U$ weight ratio 147 are relatively constant with increasing pressure. As such, operating conditions of the thermal pyrolysis reactor may be adjusted to enhance the acetylene yield for a pyrolysis feed.

Further, as it may be appreciated, different types of pyrolysis reactors may have different heat profiles. That is, some embodiments of pyrolysis reactors may operate in an isothermal manner with the heat profile being relatively constant, as noted above. However, other pyrolysis reactors may have a heat profile that is similar to a Gaussian curve. For example, a regenerative reactor may be characterized by an initial and final temperature of 300° C. and a peak pyrolysis gas temperature of 1700° C. for a residence time of 35 ms (≤10 ms at temperature≥1000° C.), the pressure effect on selectivity is even more dramatic as shown in Table 5 below.

The variations of pressure at high-severity operating conditions for a regenerative reactor are described below in Table 5 and FIGS. 1E and 1F. Table 5 includes simulation results for different ratios of reactor products produced at different pressures for different temperatures from a methane feed. Pyrolysis, in this example, is carried out under regenerative conditions resulting in a Gaussian-like temperature profile with inlet and outlet around 300° C. and with peak temperature of 1704° C. in one set of simulations and of 1783° C. in the other. About 25% of the residence time of the regenerative pyrolysis profile is at temperature above 1200° C. The pyrolysis of this example is carried out with 2:1 molar diluent of hydrogen in a methane feed, and at various reactor pressures between 3 psig (21 kPag) and 162 psig (1117 kPag). All products larger than $C_2$ are considered as $C_3^+$ in this example and the product is the reaction product yield from the converted pyrolysis feed.

TABLE 5

70% Regenerative Conversion Data

| Peak Temp (° C.) | Pres. (psig) | time (sec) | Conv. | Products (weight percent) | | | | | $C_2U$ | $C_3^+/C_2U$ | E/A |
|---|---|---|---|---|---|---|---|---|---|---|---|
| | | | | $H_2$ | $CH_4$ | $C_2H_2$ | $C_2H_4$ | $C_3^+$ | | | |
| 1704 | 3 | 0.034 | 70% | 30.4 | 24.3 | 34.3 | 3.0 | 7.9 | 37.3 | 0.21 | 0.09 |
| 1704 | 15 | 0.034 | 72% | 30.7 | 22.2 | 33.6 | 5.0 | 8.4 | 38.6 | 0.22 | 0.15 |
| 1704 | 29 | 0.034 | 74% | 30.7 | 21.2 | 31.6 | 7.4 | 8.8 | 39.0 | 0.23 | 0.24 |
| 1704 | 36 | 0.034 | 74% | 30.6 | 21.0 | 30.5 | 8.5 | 8.9 | 39.0 | 0.23 | 0.28 |
| 1704 | 59 | 0.034 | 74% | 30.3 | 21.1 | 26.8 | 11.6 | 9.2 | 38.4 | 0.24 | 0.43 |
| 1704 | 103 | 0.034 | 71% | 29.4 | 23.1 | 20.1 | 15.6 | 9.1 | 35.7 | 0.26 | 0.78 |
| 1704 | 162 | 0.034 | 66% | 28.1 | 27.5 | 13.5 | 17.2 | 8.6 | 30.7 | 0.28 | 1.27 |
| 1783 | 15 | 0.011 | 67% | 30.0 | 26.5 | 33.4 | 3.0 | 7.1 | 36.3 | 0.20 | 0.09 |
| 1783 | 36 | 0.011 | 69% | 30.2 | 24.5 | 32.5 | 5.0 | 7.6 | 37.5 | 0.20 | 0.15 |
| 1783 | 44 | 0.011 | 70% | 30.2 | 24.2 | 31.9 | 5.8 | 7.8 | 37.6 | 0.21 | 0.18 |
| 1783 | 74 | 0.011 | 70% | 30.1 | 23.7 | 29.4 | 8.3 | 8.0 | 37.7 | 0.21 | 0.28 |
| 1783 | 103 | 0.011 | 70% | 29.8 | 23.8 | 26.7 | 10.6 | 8.1 | 37.3 | 0.22 | 0.40 |
| 1783 | 162 | 0.011 | 69% | 29.2 | 25.0 | 21.8 | 13.9 | 8.1 | 35.6 | 0.23 | 0.64 |

As shown in Table 5, as pressure increases from 3 psig (21 kPag) to 162 psig (1117 kPag), $C_2U$ yields decrease at a slow rate from 37 wt % to 31 wt % for a 33 ms residence time in a temperature profile that peaks at 1704° C. However, the E/A weight ratios increase rapidly with the increase in pressure. For the profile having peak temperature of 1784° C. and an 11 ms residence time, the $C_2U$ yields are roughly constant at about 37 wt %, while the E/A weight ratio again increases with increasing pressure. Accordingly, the higher pressures tend to lead to higher E/A weight ratios, while the $C_3^+$ levels at these different temperatures and pressures remain relatively constant at around 8 wt % for the two profiles. As a result, the $C_3^+$ to $C_2U$ weight ratio increases at slow rate for these different temperatures with the higher temperature providing roughly constant $C_3^+$ to $C_2U$ weight ratio, but the E/A weight ratio increases at a larger rate. Moreover, higher pressures do not have a significant impact on $C_3^+$ levels as the $C_3^+$ to $C_2U$ weight ratio remains almost constant, which is an enhancement over the isothermal reactors.

From this table, the regenerative reactor may be utilized to further optimize the distribution the yield of $C_2U$ (e.g., acetylene yield relative to the ethylene yield) for certain operating conditions. That is, a specific pressure, temperature and residence time may be utilized to optimize the distribution of $C_2U$ yield along with the heat profile of the reactor. These operating conditions may be characterized by the $C_3^+$ to $C_2U$ weight ratio along with an E/A weight ratio, which may be further explained in view of the FIGS. 1E and 1F.

Figure 1E:
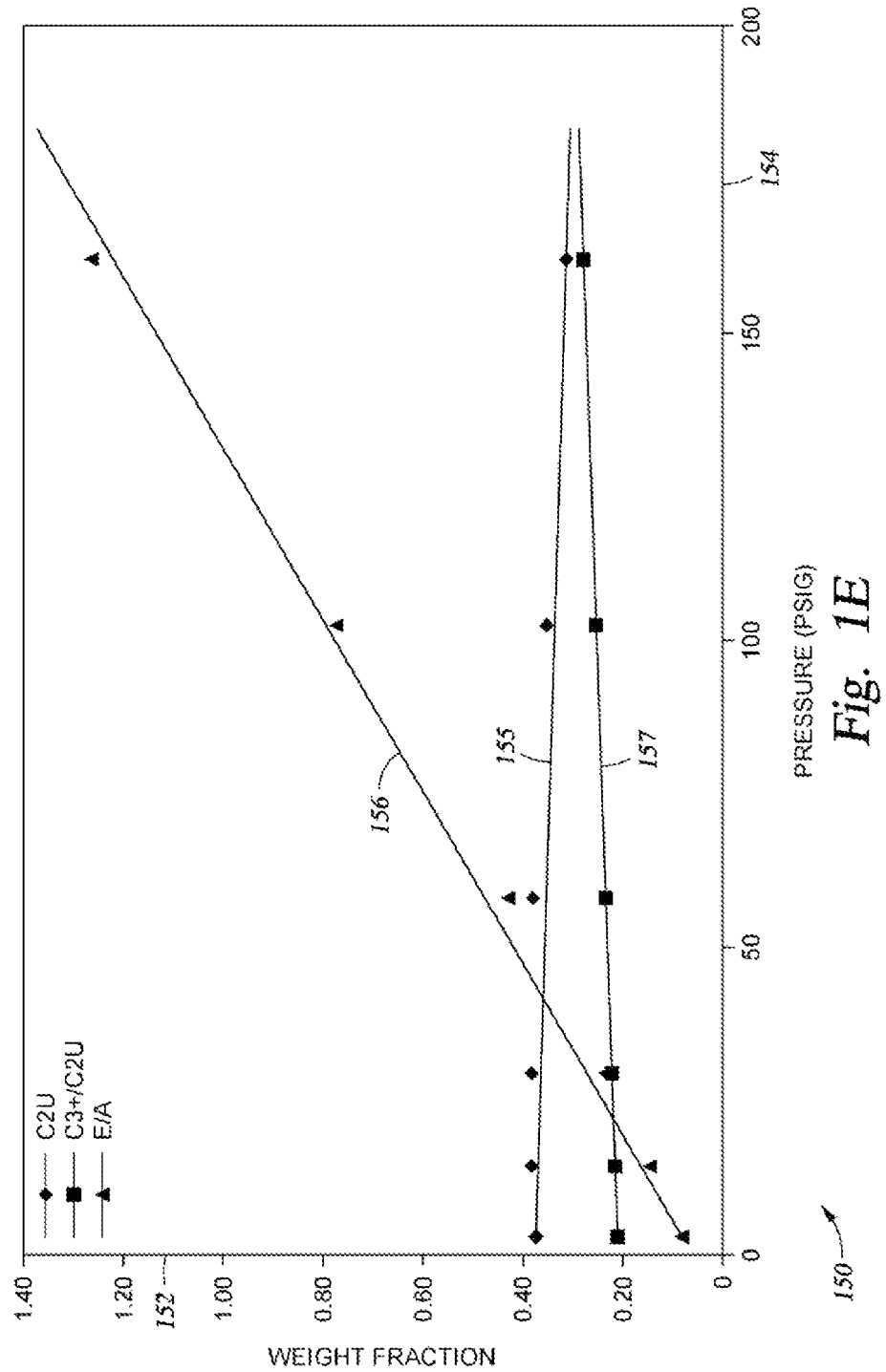
Figure 1F:
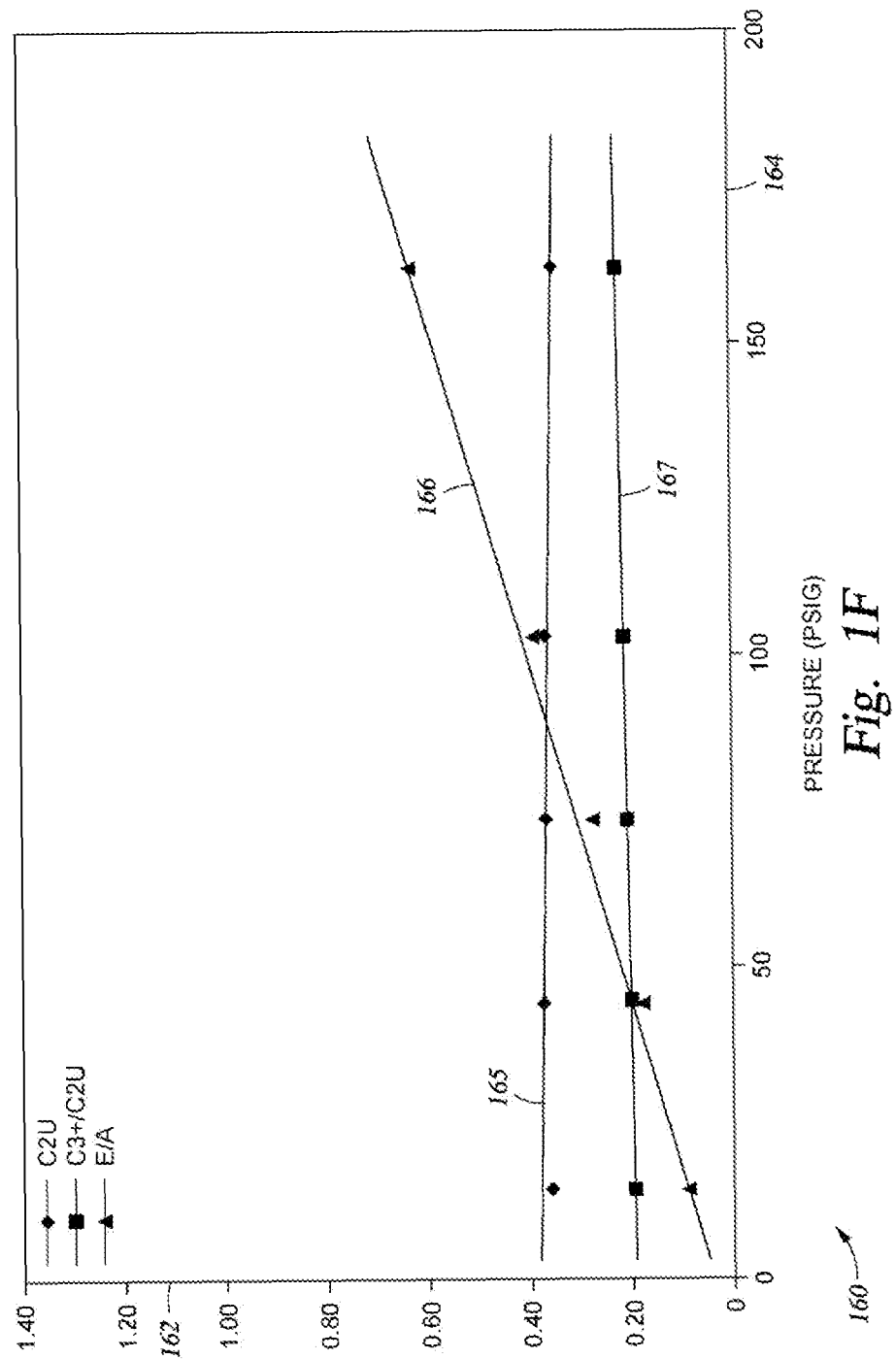

FIGS. 1E and 1F illustrate that the simulation results for different ratios of reactor products produced at different pressures for certain temperatures from a methane feed. The results of operating at the various pressures are provided for comparison of the product yields achievable at the residence times associated with the $C_2U$ yield and E/A weight ratio for that pressure. Pyrolysis, in this example, is carried out under regenerative reactor thermal conditions, with 2:1 molar diluent of hydrogen in a methane feed, and with a peak temperature of 1704° C. for diagram 150 and of 1784° C. for diagram 160. All products larger than $C_2$ are considered as $C_3^+$ in this example and the product is the reaction product yield from the converted pyrolysis feed. In diagram 150, certain values for $C_2U$ yield 155 in wt % of the product, ethylene to acetylene weight ratio 156, and $C_3^+$ to $C_2U$ weight ratio 157 are shown in weight fraction (or weight ratio) along the Y-axis 152 for various pressures (in psig) along the X-axis 154. The ethylene to acetylene weight ratio 156 and $C_3^+$ to $C_2U$ weight ratio 157 increases with increasing pressure, while the $C_2U$ yield 155 decreases slightly with increasing pressure. Similarly, in diagram 160, certain values for $C_2U$ yield 165 in wt % of the product, ethylene to acetylene weight ratio 166, and $C_3^+$ to $C_2U$ weight ratio 167 are shown in weight fraction (or weight ratio) along the Y-axis 162 for various pressures (in psig) along the X-axis 164. The ethylene to acetylene weight ratio 166 increases with increasing pressure, while the $C_2U$ yield 165 and $C_3^+$ to $C_2U$ weight ratio 157 are relatively constant with increasing pressure. As such, operating conditions of the regenerative thermal pyrolysis reactor may be adjusted to enhance the distribution of the ethylene yield and/or acetylene yield for a pyrolysis feed.

In addition, it is beneficial to maintain longer residence times and lower temperatures to maximize E/A weight ratio. However, such residence times and temperatures result in higher weight ratios of $C_3^+$ to $C_2U$. Accordingly, the design and operating conditions may be adjusted to provide a balance between the E/A weight ratio and the $C_3^+$ to $C_2U$ weight ratio. For example, a thermal pyrolysis reactor may be operated at lower temperatures to maximize the E/A weight ratio at an efficient and operable $C_3^+$ to $C_2U$ weight ratio. For instance, the operation of the pyrolysis unit and hence operating conditions may be optimized based on objectives for the pyrolysis unit performance. As an example, the operating conditions, such as the peak pyrolysis gas temperatures and/or pressure, of the thermal pyrolysis reactor may be adjusted based on an optimized value from an optimization function that comprises an ethylene to acetylene weight ratio and the $C_3^+$ to $C_2$ unsaturate weight ratio. In another example, when the objective is a high E/A weight ratio, the pyrolysis reactor may be optimized by (i) using a regenerative thermal reactor or other reactor having Gaussian-like temperature profile, (ii) increasing design operating temperature to be above a minimum level needed to achieve an acceptably low value of $C_3^+/C_2U$ (which may be referred to as a coke operability limit), and then (iii) increasing design operating pressure as much as possible given other reactor and system constraints. In another example, if the objective is a product with a minimal E/A weight ratio, the reactor may be optimized by (i) using a reactor that gives a isothermal temperature profile, (ii) operating the reactor at the lower end of the preferred pressure range, such as from about 4 psig (27 kPag) to about 59 psig (407 kPag), and (iii) increasing temperature as much as possible within the reactor materials constraints.

The pyrolysis reactors may be limited to certain pressures by various limitations. For example, at higher pressures and constant residence times, mass density of the gas increases and thus thermal reactors require higher heat transfer rates per unit of reactor volumes. This heat transfer rate may exceed the capability of the reactor internals or may lead to exceedingly small channels or exceedingly large numbers of channels per square inch (CPSI). Thus, these limitations may eventually lead to impractical reactor dimensions and impractically high levels of pressure drop.

Unless otherwise stated, all percentages, parts, ratios, etc., are by weight. Unless otherwise stated, a reference to a compound or component includes the compound or component by itself, as well as in combination with other compounds or components, such as mixtures of compounds.

Further, when an amount, concentration, or other value or parameter is given as a list of upper preferable values and lower preferable values, this is to be understood as specifically disclosing all ranges formed from any pair of an upper preferred value and a lower preferred value, regardless whether ranges are separately disclosed.

The terms "convert" and "converting" are defined broadly herein to include any molecular decomposition, cracking, breaking apart, conversion, and/or reformation of organic molecules (hydrocarbons) in the feed, by means of at least pyrolysis heat, and may optionally include supplementation by one or more of catalysis, hydrogenation, diluents, and/or stripping agents.

As used herein, the expression "non-volatiles" may be defined broadly herein to mean substantially any resid, metal, mineral, ash, ash-forming, asphaltenic, tar, coke, and/or other component or contaminant within the feedstock that does not vaporize below a selected boiling point or temperature and which, during or after pyrolysis, may leave an undesirable residue or ash within the reactor system, which is difficult to remove. Noncombustible nonvolatiles may include ash, for example. Methods for determining asphaltenes and/or ash may include American Society of Testing and Materials (ASTM) methods, such as methods for asphaltenes may include ASTM D-6560 and D-7061 and methods for ash may include ASTM D-189, D-482, D-524, and D-2415.

As used herein, the terms "coke" and "soot" may refer to hydrocarbonaceous material that accumulates within the reactor during pyrolysis or to solid-phase hydrocarbonaceous materials that emerge from the reactor with pyrolysis effluent. The hydrocarbonaceous material that accumulates within the reactor during pyrolysis may also be defined as the fraction of the pyrolysis feed that remains in a thermal pyrolysis reactor and thus does not emerge from the reactor as pyrolysis effluent. Coke and soot are components of the reactor product, which are included for $C_3^+$ product for pyrolysis selectivity. The term "$C_3^+$" means all products of the pyrolysis feed having more than three carbon atoms, which include coke and soot, whether those products emerge from the reactor or remain within the reactor. The reactor product that does emerge may be referred to as the reactor effluent, which is at least a portion of the reactor product.

The term "pyrolysis feed" means the composition, which may be a mixture, subjected to pyrolysis. In one embodiment, the pyrolysis feed is derived from a hydrocarbon feed (e.g., by separation of a portion from the hydrocarbon feed and optional addition of diluents.

As used herein, the "hydrocarbon feed" contains hydrocarbons (C bound to H) and may contain (i) minor components of heteroatoms (<10 wt %) covalently bound to hydrocarbons and (ii) minor components of heteroatoms (<10 wt %) not bound to hydrocarbons (e.g., $H_2O$), wherein these weight percents are based on the weight of the hydrocarbon feed. The term "hydrocarbons in the hydrocarbon feed" or "hydrocarbons of the hydrocarbon feed" means molecules within the hydrocarbon feed that contain at least hydrogen and carbon and, optionally, heteroatoms covalently bound to a portion of such molecules. Weight percents of hydrogen and carbon, as used to characterize the hydrocarbon feed, are provided as a percent of the hydrocarbons in the hydrocarbon feed. The hydrocarbon feed may include, by way of non-limiting examples, one or more of Fischer-Tropsch gases, methane, methane containing streams such as coal bed methane, biogas, associated gas, natural gas and mixtures or components thereof, steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, hydrocarbon streams derived from plant or animal matter, and/or any mixtures thereof.

As used herein, the expression "advantaged feed" means a feed that has a lower cost (per ton or per heating value) than Brent reference crude oil and may include, by way of non-limiting examples, one or more methane containing feeds and one or more high-aromatic containing streams. Some examples may include one or more of Fischer-Tropsch gases, methane, methane containing streams such as coal bed methane, biogas, associated gas, natural gas and mixtures or components thereof, steam cracked gas oil and residues, gas oils, coker naphtha, steam cracked naphtha, catalytically cracked naphtha, hydrocrackate, reformate, raffinate reformate, natural gasoline, Fischer-Tropsch liquids, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, and/or any mixtures thereof.

The term "hydrogen content" means atomic hydrogen bound to carbon and/or heteroatoms covalently bound thereto and which excludes molecular hydrogen ($H_2$) in the hydrocarbon feed expressed as a weight percent based on the weight of the hydrocarbons in the hydrocarbon feed. Hydrogen content as applied to pyrolysis feed or reactor feed are expressed as a weight percent of hydrocarbons in the respective feed. A hydrocarbon feed may have a hydrogen content in the range of 6 wt % (weight percent) to 25 wt %, 8 wt % to 20 wt % (e.g., not natural gas), or 20 wt % to 25 wt % (e.g., natural gas). The hydrogen content of hydrocarbon feeds, reactants and products for present purposes can be measured using any suitable protocol, e.g., ASTM D4808-01(2006) Standard Test Methods for Hydrogen Content of Light Distillates, Middle Distillates, Gas Oils, and Residua by Low-Resolution Nuclear Magnetic Resonance Spectroscopy or ASTM D5291-10 Standard Test Methods for Instrumental Determination of Carbon, Hydrogen, and Nitrogen in Petroleum Products and Lubricants. The hydrocarbon feed may be provided directly as a pyrolysis feed, may optionally be mixed with a diluent feed to form a pyrolysis feed, or may have a portion of the hydrocarbon feed removed (e.g., removal of nonvolatiles at the operating conditions of the reactor) to form a pyrolysis feed. That is, the pyrolysis feed may be derived from the hydrocarbon feed. A pyrolysis feed may include hydrogen gas ($H_2$) in an amount that provides a preferred ratio of hydrogen gas ($H_2$) moles to the total moles of carbon (C) in the hydrocarbon components of the pyrolysis feed. The ratio of hydrogen to carbon ($H_2$/C) may be from 0.0 or 0.1 to 5.0, such as 0.0, 0.1, 1.0, 2.0, 3.0, 4.0, 5.0, or values in between. Combining the hydrogen content of the hydrogen gas to the hydrogen and carbon contents of the hydrocarbon components of the pyrolysis feed may result in a weight percent of total hydrogen in the pyrolysis feed that is greater than that in the hydrocarbon feed. For example, the weight percent of total hydrogen in a pyrolysis feed may be between 8 wt % and 54 wt %.

As used herein, the expression "combustion feed" means the two or more individual feeds that are to be combined to form a combustion reaction or a mixture of two or more feeds, such as a combustion fuel that does not contain oxidants (e.g., $O_2$) or non-combustible non-volatiles and a combustion oxidant that may include an oxygen or oxygen containing fluid. The combustion fuel may include, by way of non-limiting examples, one or more of Fischer-Tropsch gases, methane, methane containing streams such as coal bed methane, biogas, associated gas, natural gas and mixtures or components thereof, synthesis gas (mixtures of CO and $H_2$) and hydrogen. The combustion oxidant may include, but are not limited to, air, oxygen or mixtures thereof. Any of the combustion feed, fuel, or oxidant may additionally include non-combustible but volatile diluents such as $N_2$, $CO_2$, $H_2O$, and/or other inert gases.

The term "reactor", as used herein, refers to equipment used for chemical conversion. As such, several items identified as reactors may be combined to become a single entity that is also identified as a reactor, in that individual and combined entities may all be characterized as equipment used for chemical conversion. The regenerative reverse-flow thermal pyrolysis reactors described herein may comprise first and second reactor entities, for example as described in U.S. Patent App. Pub. No. 20070191664.

The term "pyrolysis reactor", as used herein, refers to a system for converting hydrocarbons by means of at least pyrolysis chemistry. As used herein, the pyrolysis reactor may include pyrolysis chemistry alone (e.g., in the absence of oxygen for the conversion), or may also include combustion chemistry, including combustion chemistry that occurs along with the pyrolysis chemistry as in a partial combustion reactor. The pyrolysis reactor may include one or more reactors and/or associated equipment and lines. A region, as used herein, refers to a location within the pyrolysis reactor, which may include one or more reactors and/or associated equipment and lines. The region may include a specific volume within a reactor, a specific volume between two reactors and/or the combination of different disjointed volumes in one or more reactors. The regenerative reverse-flow thermal pyrolysis reactors described herein may comprise first pyrolysis reactor and second pyrolysis reactor, for example as described in U.S. Patent App. Pub. No. 20070191664.

As used herein, the "thermal pyrolysis reactor" includes at least predominantly pyrolysis chemistry. Pyrolysis or pyrolysis chemistry, such as the conversion of hydrocarbons to unsaturates such as ethylene and acetylene, is an endothermic process requiring addition of heat. The terms crack and cracking may be used interchangeably with the terms pyrolyse and pyrolysis. In a thermal pyrolysis reaction, ≥50%, ≥80%, or≥90%, of this heat is provided by heat transfer via solid surfaces such as tubulars or bed materials. Any combustion chemistry that occurs within the pyrolysis stream of a thermal pyrolysis reactor provides a minority of the endothermic heat of pyrolysis, such as<50%, <20%, or<10% of the endothermic heat of pyrolysis.

The term "high-severity operating conditions" means pyrolysis conditions resulting in the conversion of the a pyrolysis feed comprising hydrocarbons to make a product having an acetylene content≥10.0 wt % based on the weight of the hydrocarbons in the pyrolysis feed. The operating conditions for a reactor may be characterized by a severity threshold temperature that divides low-severity operating conditions in reactors from high-severity operating conditions in reactors. The severity threshold temperature is defined as the lowest temperature at which the feed to the reactor may react at a residence time≤0.1 sec (second) to make at least 10 wt % acetylene as a percent of the hydrocarbons in the feed evaluated at the given operating conditions of the process. The high-severity operating conditions for a thermal pyrolysis reactor may be characterized as peak pyrolysis gas temperatures that are greater than the severity threshold temperature. The low-severity thermal pyrolysis reactor may be characterized as pyrolysis gas temperatures that are less than the severity threshold temperature and no pyrolysis gas temperatures that exceed the severity threshold temperature. For example, for the thermal conversion of methane at a pressure of 14.7 psig (101 kPag) and with 2:1 molar ratio of hydrogen diluent, the threshold temperature is about 1274° C. for this process. At temperatures at or above 1274° C., yields of acetylene can exceed 10 wt % of the starting methane, at some time≤0.1 seconds. Conversely, at temperatures below 1274° C., there are no times≤0.1 seconds for which yields of acetylene reaches 10 wt % of the starting methane. A similarly-defined severity threshold temperature may be used to distinguish between high-severity and low-severity types of other reactors, such as partial combustion, indirect combustion, and arc processes. That is, if that reactor operation is capable of converting the hydrocarbons in the feed to≥10% acetylene at a residence time of≤0.1 seconds, that reactor is considered a high-severity reactor.

The term pyrolysis reactor type means one of the following pyrolysis reactor types of partial combustion, indirect combustion, arc process and thermal pyrolysis. The types of pyrolysis reactors can be divided into eight different types: low-severity partial combustion, high-severity partial combustion, low-severity indirect combustion, high-severity indirect combustion, low-severity arc process, high-severity arc process, low-severity thermal pyrolysis and high-severity thermal pyrolysis. These pyrolysis reactor types differ in the means of generating and transferring the heat for the pyrolysis and/or in the severity utilized in the operating conditions.

According to one or more embodiments of the present techniques, an enhanced process that utilizes two different reactor types, is provided for the production of $C_2U$ (e.g., acetylene and ethylene), which are useful for manufacturing polyolefins and other petrochemical products. The process may include various stages, such as feed preparation, pyrolysis, recovery and further processing, such as separation of the polymer grade monomer and polymerization to polyethylene. The two different reactor types include at least one high-severity pyrolysis reactor (high-severity partial combustion, high-severity indirect combustion, high-severity arc process and high-severity thermal pyrolysis) and a second reactor type, which may be any other high-severity pyrolysis reactor or any of the low-severity pyrolysis reactor types (low-severity partial combustion, low-severity indirect combustion, low-severity arc process and low-severity thermal pyrolysis). The high-severity pyrolysis reactor may be utilized to expose a first pyrolysis feed to peak pyrolysis gas temperatures equal to or above 1400° C. or equal to or above 1540° C. for a thermal pyrolysis reactor. Optionally, the high-severity pyrolysis reactor may have operating conditions that are below a specific selectivity threshold, such as a $C_3^+$ to acetylene weight ratio≤0.5, ≤0.45, or≤0.4. Operation at low levels of $C_3^+$/acetylene is desirable both to improve process economics and to improve process operability. Economics are improved by low $C_3^+$/acetylene weight ratio because $C_3^+$ products produced by high-severity pyrolysis are less valuable than the acetylene product. Further, operability is improved by low $C_3^+$/acetylene weight ratio because $C_3^+$ products may include substantial amounts of coke, whose production may hinder operations. At least a portion of the reactor products from the respective reactors may be combined and processed together as noted further below. This effluent may be further processes to recover polyethylene, polypropylene, benzene, polyolefins or other final conversion products.

Pyrolysis reactors do not include reactors that operate conditions that may have high E/A weight ratios, but very low yields of $C_2U$, such as partial oxidation syngas reactors, cokers or heat soakers. Pyrolysis reactors preferentially operate at conditions that yield $C_2U$ at a level 1 wt %, ≥5 wt % or even≥10 wt % in the reactor product. The pyrolysis reactor may be characterized by a severity threshold temperature that divides low-severity pyrolysis reactors, as noted above. This severity threshold method may be applied to distinguish between high-severity and low-severity for any of the reactor types.

Each high-severity pyrolysis reactor type may have advantages or disadvantages relative to each other. For instance, the partial oxidation reactor produces syngas or CO, as a major product. The arc pyrolysis reactor products may not be contaminated by combustion products, but may be disadvantaged if a low cost electric power supply is not available. Also, both the partial oxidation reactor and arc reactor may be amenable to resid containing feeds due to a close coupled active quench step where the non-combustible non-volatiles are conducted away via the quench media. Thermal pyrolysis reactors may avoid both the air separation capital expense, heat loss associated with an active quench, and/or may provide more effective management of certain impurities when combustion products are not preferred. However, thermal pyrolysis reactors may have coking problems in pyrolysis reactor channels, which may result in excess amounts of heat release or reduced flow depending on the specific thermal reactor.

Similarly, the low-severity pyrolysis reactors also may have advantages or disadvantages relative to each other. For instance, the low-severity reactors may be useful to crack certain types of feeds, such as a $C_2^+$ saturate containing feed, which $C_2^+$ saturates may be≥50 wt %, ≥60 wt %, or≥90 wt % of the hydrocarbons in the feed. The $C_2^+$ saturate containing feed may include saturate containing feeds heavier than methane (e.g., ethane, naphtha or light gasoil). In these low-severity operating conditions, reactor effluents may advantageously yield higher levels of ethylene and propylene. The low-severity pyrolysis reactor may operate under operating conditions that maximize olefin yields of saturate containing feed streams; typically between 700° C. and 1200° C. at residence times between 0.01 to 2 second.

Accordingly, the present techniques may involve operating the two or more different types of pyrolysis reactors with at least one of these being a high-severity pyrolysis reactor. These operating conditions may include adjusting operational settings to adjust the pressure within a reactor and/or the temperature within a reactor. The operational settings may include increasing the heat generated by providing different combustion feeds to the respective pyrolysis reactor. The present techniques may be further understood with reference to the FIGS. 2 to 5, which are discussed below.

Figure 2:
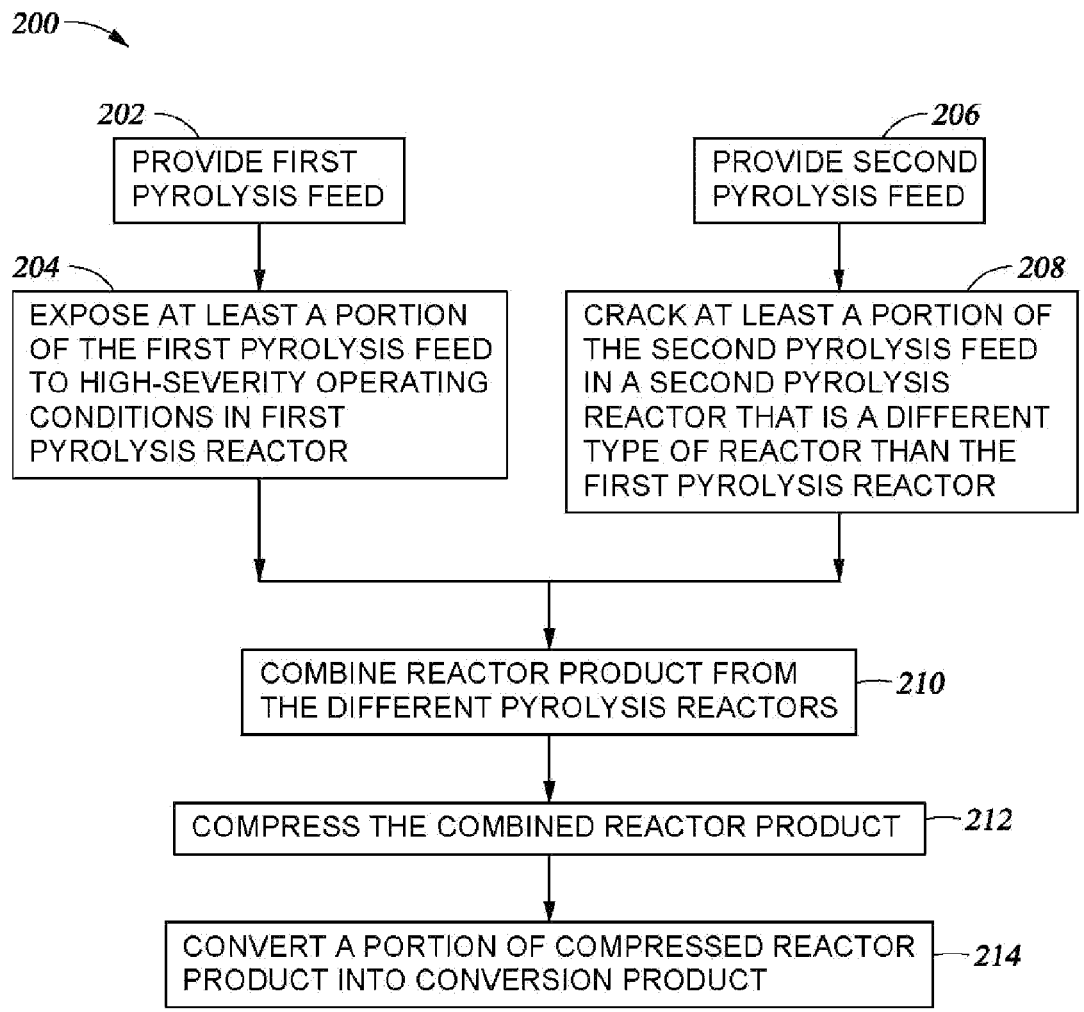
FIG. 2 is a simplified process flow diagram illustrating an embodiment of the present techniques.

To begin, an exemplary embodiment of the present techniques is illustrated in the block flow diagram 200 of FIG. 2. In this flow diagram 200, a process for the production of conversion products, such as ethylene, propylene, and/or polyolefins, is disclosed, which includes various stages. For instance, a feed preparation stage is described in block 202 and 206. A cracking stage is described in blocks 204 and 208, which involves cracking a first pyrolysis feed in a first pyrolysis reactor and a second pyrolysis feed in a second pyrolysis reactor, which is different from the first pyrolysis reactor. The respective reactor products from the reactors may be processed together in an enhanced manner. Then, a recovery stage is described in blocks 210 to 214, which further processes the reactor product or reactor effluent from the reactor to recover a conversion product.

At block 202, a first pyrolysis feed is provided to a first pyrolysis reactor. The first pyrolysis feed may be derived from a hydrocarbon feed, which may include one or more of methane, natural gas, petroleum or petrochemical liquids and mixtures thereof, for example. The hydrocarbon feed may be subjected to various feed preparation processes to form the first pyrolysis feed. That is, the feed preparation processes optionally include removal of impurities or contaminants prior to providing the first pyrolysis feed to the first pyrolysis reactor. The feed preparation process may include mixing the hydrocarbon feed with a diluent feed, one or more of condensate and water removal units, acid gas removal units (e.g., caustic or amine treater units), dehydration units (e.g., glycol units), nitrogen removal units, hydrogenation, demetalation, visbreaking, coking and/or vapor/liquid separators. The impurities or contaminants, which may include one or more of carbon dioxide, carbon monoxide, sulfur species, oxygenates and non volatiles (e.g., metal), may be conducted away from the process. As a first example, the hydrocarbon feed may comprise crude oil and crude oil components. As a second example, the pyrolysis feed may comprise substantially methane (e.g., ≥50 wt %, ≥75 wt %, or≥90 wt % of the pyrolysis feed).

In block 204, the first pyrolysis feed is exposed to high-severity operating conditions in the first pyrolysis reactor. The exposure of the high-severity operating conditions may involve cracking a portion of the first pyrolysis feed to create a first reactor product. The reactor product includes one or more $C_2U$, and optionally includes hydrogen ($H_2$), methane, ethane, methyl acetylene, diacetylene, and $C_3^+$ products (e.g., benzene, tars, soot, etc.). The reactor product includes components that emerge from the reactor and those that remain within the reactor, if any, as a result of pyrolysis (e.g., coke may remain in the reactor and later emerge as a portion of the combustion products). The amount of coke remaining in the reactor may be determined from a mass balance of the process. Further, the first pyrolysis reactor may include any one of the high-severity pyrolysis reactors, such as a high-severity partial combustion reactor, high-severity indirect combustion reactor, high-severity arc process reactor and high-severity thermal pyrolysis reactor. As a specific example, the first pyrolysis reactor may be a regenerative reverse flow reactor, as described in U.S. Patent App. Pub. No. 20070191664. Other embodiments may include pyrolysis reactors as described in U.S. Pat. No. 7,491,250, U.S. Ser. No. 61/349,464 and U.S. Patent App. Pub. Nos. 20070144940 and 20080142409. Regardless of the specific type of thermal pyrolysis reactor, it may operate at peak pyrolysis gas temperatures between 1200.0° C. and 2200.0° C., preferably between 1400.0° C. to 1900.0° C. In particular, for reactors with an isothermal heat profile, the temperatures may be between 1450.0° C. and 1700.0° C., or between 1540.0° C. and 1650.0° C. For reactors with a Gaussian like heat profile, the peak pyrolysis gas temperatures may be between 1540.0° C. and 2200.0° C. or 1600.0° C. and 1800.0° C. For a regenerative reverse flow reactor, it may be operated to have a cycle time of the combustion step and the pyrolysis step that is between 0.5 second to 30 seconds.

At block 206, a second pyrolysis feed is provided to a second pyrolysis reactor. The second pyrolysis feed may be derived from a hydrocarbon feed, which may include one or more of methane, natural gas, petroleum or petrochemical liquids and mixtures thereof, for example. The second pyrolysis feed, similar to the first pyrolysis feed, may be subjected to various feed preparation processes to form the pyrolysis feed from a hydrocarbon feed.

In block 208, at least a portion of the second pyrolysis feed is cracked in the second pyrolysis reactor. The portion of the second pyrolysis feed may be converted into a second reactor product. Similar, to the discussion above with regard to the first reactor product, the second reactor product may include one or more $C_2U$, and optionally includes hydrogen ($H_2$), methane, ethane, methyl acetylene, diacetylene, and $C_3^+$ products (e.g., benzene, tars, soot, etc.). Further, the second pyrolysis reactor may include any of the other reactor types that are different from the first pyrolysis reactor. That is, the second pyrolysis reactor may include any one of other high-severity pyrolysis reactor types or any of the low-severity pyrolysis reactors, such as a low-severity partial combustion reactor, a low-severity indirect combustion reactor, a low-severity arc process reactor and a low-severity thermal pyrolysis reactor.

At least a portion of the first reactor product and at least a portion of the second reactor product may be conducted away for storage or further processing. Optionally, one or more upgrading processes may be included in the recovery stage, as shown in blocks 210 to 214. For instance, the at least a portion of the first reactor product and the at least a portion of the second reactor product may be combined and subjected to various processes in the recovery stage in blocks 210 to 214. At block 210, the first reactor product from the first reactor and the second reactor product from the second reactor may be combined into one reactor product stream, which may be referred to as a combined reactor product. These reactor products may be combined, in a combining unit for example, before or after one of the reactor products from the respective reactors is subjected to one or more separation processes. The combining unit may be a manifold, mixing vessel, line coupling or other suitable region or coupling of these reactor products. Also, the first reactor product from the first reactor, second reactor product from the second reactor or combined reactor product may be subject to separation processes to provide a bottoms product. The separation may remove one or more bottom products comprising solids, such as higher boiling point materials (e.g., contaminates, solids or impurities) from the $C_2U$ in reactor product. The separation process may include a tar and/or solid removal process, compression, adsorption, distillation, washing, and drying of the remaining reactor product, and/or any combination of one or more of these processes. For low-severity, the separation process may include a vapor/liquid separator (e.g., flash drum) or primary fractionator or other suitable distillation. Then, at block 212, the combined reactor product may be compressed. The compression may include compressors that operate at outlet pressures pressure from 50 psig (345 kPag) to 400 psig (2758 kPag), or from 150 psig (1034 kPag) to 300 psig (2068 kPag).

At block 214, the combined reactor product may optionally be provided to a conversion process. The combined reactor product may be in liquid phase, vapor phase or a mixture thereof, and may be subjected to a conversion process that is performed by a catalyst in the liquid phase, vapor phase or a mixture thereof. For instance, the conversion process may include an acetylene or methyl acetylene conversion process, which may include acetylenes hydrogenation in an isothermal, slurry or adiabatic catalytic reactor, or other suitable conventional techniques. The catalytic reactor may employ group VI or VIII catalyst, catalyst bimetal or trimetal blends on an alumina, silica or other support, as is well known in the art. For example, the acetylene in the reactor product is absorbed into a liquid, hydrogenated within that liquid and then the ethylene product is desorbed from the liquid. As another example, the conversion process may include a propylene conversion process.

Further, the conversion products, which may include ethylene or propylene, may optionally be provided to a purification or upgrading process. Should additional upgrading or purification of the conversion products be desired, purification systems, such as that found in *Kirk-Othmer Encyclopedia of Chemical Technology*, 4th edition, Volume 9, John Wiley & Sons, 1996, pg. 894-899, may be used. In addition, purification systems, such as that described in *Kirk-Othmer Encyclopedia of Chemical Technology*, 4th edition, Volume 20, John Wiley & Sons, 1996, pg. 249-271, may also be used. Other examples may be found in U.S. Pat. Nos. 6,121,503; 5,960,643; 5,364,915; 5,238,892; 5,280, 074; 5,288,473; 5,102,841; 4,956,426; 4,508,842; and EP Patent No. 0612753; and EP Patent No. 0012147.

Optionally, the upgraded product is conducted away for storage or for further processing, such as conversion into polyethylene or polypropylene. For instance, the purification process may include (multistage) distillation or refrigerated distillation including a depentanizer, a debutatizer, C4 separation and conversion, hydrotreaters, a demethanator tower and $C_2$ splitter. Further, olefin polymerization may include both the gas phase and solution polymerization methods, which conventional processes and may be employed in the practice of the present techniques. As an example, U.S. Pat. Nos. 6,822,057; 7,045,583; 7,354,979 and 7,728,084 describe different ethylene polymerization processes that may be utilized.

Optionally, the ethylene product may be provided for other processes or used commercially as a final product. These processes may include generating ethylene glycol or other products. As an example, the ethylene stream may be treated, separated and polymerized to form plastic compositions, which may include polyolefins, particularly polyethylene. Any conventional process for forming polyethylene may be used, while catalytic processes are preferred. Particularly preferred are metallocene, Ziegler/Natta, aluminum oxide and acid catalytic systems. Examples may include U.S. Pat. Nos. 3,258,455; 3,305,538; 3,364,190; 5,892,079; 4,659,685; 4,076,698; 3,645,992; 4,302,565; and 4,243,691. In general, these methods involve contacting the ethylene product with a polyolefin-forming catalyst at a pressure and temperature effective to form the polyolefin product.

Beneficially, this configuration provides a more efficient process to recover olefins by integrating different pyrolysis reactor types. For instance, in this configuration, one of the enhancements is the flexibility in the hydrocarbon feed utilized for olefin recovery. That is, any hydrocarbon feed provided may be separated into different streams for different reactors, such as the first pyrolysis reactor and the second pyrolysis reactor. For instance, the first pyrolysis feed may be derived from a broader range of hydrocarbon feeds with lower hydrogen contents and advantaged feeds (e.g., heavy aromatic to methane), while the second pyrolysis feed may be derived from specific feeds which may not require the high-severity operating conditions, e.g., saturates. These advantaged feeds, which do not typically react in at low-severity condition or react to lower value products, react in the process to provide $C_2U$. Higher severity, as provided in the present process, converts at high levels aromatic containing and/or methane containing feeds to valuable $C_2$ products. Various combinations of different pyrolysis reactors may be envisioned, where each type of pyrolysis reactor may efficiently crack a preferred portion of a hydrocarbon feed. As such, a group of pyrolysis reactors may be coupled together with each associated with different portions of the hydrocarbon feeds, which typically foul or are unreactive in other process.

As a first example, a high-severity pyrolysis reactor may be used with a low-severity reactor. For instance, a reverse flow regenerative reactor may be the high-severity pyrolysis reactor and a steam cracking reactor may be the low-severity pyrolysis reactor. This type of low-severity pyrolysis reactor and associated units may typically crack crude fractions, such as naphthas or light gas oils, while the high-severity pyrolysis reactor may be used to convert waste products and/or fuel products, such as methane, vacuum gas oils or aromatic fuel oils, to chemical products. Accordingly, with this type of embodiment, different crude fractions may be provided to two or more different pyrolysis reactors to maximize the light olefin yield (e.g., acetylene and/or ethylene) at the lowest operating cost. Further, the proposed configuration may be used to manage the dilution of the acetylene content in the reactor product from the high-severity reactor with the other reactor product (e.g., ethylene concentration) from the other reactor to maintain the acetylene concentration below the acetylene decomposition curve for a given pressure and temperature. That is, the different reactors may have the products combined to manage the recovery stage processing for different products.

As another example, a high-severity pyrolysis reactor may be used with another high-severity reactor of a different type. If utilizing two high-severity reactors, the $C_2U$ (e.g., acetylene and ethylene) of the reactor products may represent $\geq 20$ wt %, $\geq 50$ wt %, $\geq 80$ wt %, or $\geq 90$ wt % of the total $C_2^+$ gas phase components of the reactor products. In this configuration, the respective reactor products, which may contain an acetylene amount that reflects a pyrolysis $C_3^+$/acetylene weight ratio of $\leq 0.45$, may be processed together in an enhanced manner. For instance, a thermal pyrolysis reactor may be the high-severity reactor and a partial oxidation or arc pyrolysis reactor may be the other high-severity pyrolysis reactor. The partial oxidation or arc pyrolysis reactor may typically crack non-volatile containing fractions, such as atmospheric resid or fuel oils (which may also include non-combustible non-volatiles), while the high-severity thermal pyrolysis reactor may be used to convert lighter fractions, such as methane or feeds having a boiling point $\leq 565°$ C. (which do not contain the non-volatiles), to chemical products. That is, this configuration may more efficiently process the entire hydrocarbon feed to provide similar products species, e.g., acetylene and ethylene. As may be appreciated, these different reactor types may be optimized, which may be based on the feed provided, to more efficiently process the hydrocarbon feed.

Further, the integration of the pyrolysis reactors may provide the additional benefit that the recovery stage may be shared between the different pyrolysis reactors. If adding one type of pyrolysis reactor to an existing pyrolysis train, the reactor products from the respective reactors may be similar to allow co-feeding of the reactor effluent to shared process equipment. This efficient use of processing equipment may be tailored to specific reaction products of a given reactor combination. This may reduce the costs of installation, while providing more effective use of the hydrocarbon feed provided to the system. As an example, in processing crude, the volatile fraction (e.g., 80 wt % of crude) may be cracked in a thermal pyrolysis reactor to produce hydrogen, ethylene and acetylene, while the non-volatile fraction (e.g., 20 wt % of the crude) may be cracked in a different reactor (e.g., partial oxidation (PDX) reactor) to produce hydrogen, ethylene, acetylene and CO. In this configuration, the impurities, such as the CO, may be managed by a shared recovery train. Accordingly, the process may include feed swapping and/or equipment sharing.

Further still, the integration may include energy integration between two pyrolysis reactors. For example, when the second pyrolysis reactor is a steam cracking reactor, the first pyrolysis reactor or second pyrolysis reactor may be used to generate steam, or may be used to heat a hydrocarbon feed prior to separation. As such, different heat integrations may be possible for the reactor.

Moreover, the proposed process provides various enhancements over previous techniques. For instance, the process provides flexibility in managing byproducts or contaminants That is, the high-severity pyrolysis reactor in the process may be operated in a manner does not involve additional stages to remove various contaminants, which improves the efficiency of the process. As an example, the process may manage impurities based on the operating conditions of the high-severity pyrolysis reactor. That is, the present techniques expose a pyrolysis feed to specific operating conditions that may be used to manage the production of coke. For example, for thermal reactors, these high-severity operating conditions may include peak pyrolysis gas temperatures $\geq 1400°$ C., or $\geq 1540°$ C. Further, certain high-severity pyrolysis reactors, such as a high-severity thermal pyrolysis reactor, may operate at operating conditions that provide a $C_3^+$ to acetylene weight ratio $\leq 0.5$, $\leq 0.45$, or even $\leq 0.4$. These high-severity operating conditions may be adjusted to manage $C_3^+$ production in the reactor process. As an example, certain impurities in the feed (e.g., asphaltenes and/or mercaptans) may be provided to the reactor and converted into acetylene, ethylene and/or coke. By exposing the feed to these high-severity operating conditions, the $C_3^+$ product, which may include coke, tar and/or coke precursors, may be burned off within the reactor and removed from the process. As a result, feeds with higher asphaltene contents may be managed through the system without the concerns of coking in conventional processes.

Other impurities, which may include but are not limited to sulfur and nitrogen containing compounds, oxygenates, Hg, salts, water, $H_2S$, $CO_2$, and $N_2$, may be removed as different products prior to or after the high-severity first pyrolysis reactor. That is, unlike other processes, the present techniques utilize operating conditions in the pyrolysis reactor to manage the impurities.

In addition, as noted above, by using high-severity conditions (e.g., higher temperatures) in the first pyrolysis stage of the process, the present techniques may enhance $C_2$ selectivity for certain reactors in the system to manage the combined reactor product. That is, the first pyrolysis stage may crack the first pyrolysis feed at residence times that are lower than other lower temperature processes. As a result, the first pyrolysis feed is more efficiently cracked and the reactor size may be smaller (e.g., less capital expense and more efficient).

Moreover, when the first pyrolysis reactor is a regenerative reverse flow reactor, the configuration may be used to control the temperature of the reactor product at the reactor outlet to a temperature between 300° C. to 500° C. That is, the process may utilize passive quenching to provide a reactor product that does not have to involve active quenching steps to lower the reactor product temperature.

In addition, for certain embodiments with the first pyrolysis reactor being a regenerative reverse flow reactor, air may be utilized instead of oxygen gas as part of the combustion process to generate heat for the first pyrolysis feed because the combustion step is a separate step from the reaction step. Accordingly, using this type of reactor may reduce capital costs and operational costs by not requiring an oxygen feed (e.g., oxygen purification facilities) and reducing units that are utilized to remove combustion products from the reactor products.

Further, the process may optionally involve other processing steps, such as separation steps that separate the combined reactor product, at least a portion of the first reactor product and/or at least a portion of the second reactor product into an acetylene-rich product and an acetylene-lean product, which may involve separating different products from the remaining reactor product in the recovery stage. The acetylene-rich product may include ≥50 wt % of the acetylene from the reactor product, ≥70 wt % of the acetylene from the reactor product, ≥85 wt % of the acetylene from the reactor product, or even≥95 wt % of the acetylene from the reactor product. The acetylene-lean product may include from 0 wt % to the remaining portion of the acetylene that is not in the acetylene-rich product. The remaining reactor product may pass through one or more separations, such as a light gas separation or a heavier separation, to remove different products from the remaining reactor product.

For example, after blocks 204 and 208, different light gas products (e.g., a portion of the light gas in the first reactor product, second reactor product or combined reactor product) may be separated as light gas products and the remaining reactor product may form an acetylene-rich product. The light gas removal process may include different separation mechanisms along with a basic wash, for example caustic wash or amine scrubbing, to conduct the light gas products away from the remaining reactor product. For other embodiments, the light gas separation mechanisms may include pressure swing adsorption, membranes, cryogenic distillation, electrochemical separation, liquid absorption and/or liquid phase absorption and light gas desorption. For a membrane, the membrane inlet pressure or the pressure swing adsorption inlet pressure may be between 150 psig (1034 kPag) and 250 psig (1724 kPag), while the liquid phase absorption and light gas desorption may be performed at pressures between 50 psig (345 kPag) and 250 psig (1724 kPag). The light gas separation mechanisms may be used to separate hydrogen, carbon monoxide, methane, nitrogen or other light gases. The light gas products, such as hydrogen and/or methane, separated from the remaining portion of the reactor product may be used as a diluent feed into the first pyrolysis reactor, a feed stripping medium, as a fuel for the first pyrolysis reactor, or as a byproduct. The light gases may contain a fraction of the methane separated from the at least a portion of the reactor product or cracked stock. Further, in some embodiments, the light gas separation may include additional stages or units to remove one or more of carbon dioxide ($CO_2$), hydrogen sulfide ($H_2S$), and water ($H_2O$) but also may include other reactive impurities. In particular, carbon dioxide and hydrogen sulfide, if present, may be removed by washing the stream with a solution of alkali or a salt of an amine or organoamine. If water is present, it may be removed by a methanol treatment, such as described in Belgian Patent No. 722,895. Other methods for removing water are adsorption and extraction by diethylene glycol. Various exemplary embodiments of this process are described further below.

Optionally, after blocks 204 and 208, a heavier product separation may conduct away a product of condensables from the reactor product from the respective reactors, which may be the first reactor product, second reactor product, or combined reactor product. The condensables may include vaporized liquids that condense, such as benzene, or are separated via cooled separations for example, adsorption, vapor liquid separators, flash drums etc.

Further, in one or more embodiments, a hydrocarbon feed may include non-volatiles, which are materials that are not in the gas phase (i.e. are components that are in the liquid or solid phase) at the temperature, pressure and composition conditions of the inlet to the reactor. Non-combustible non-volatiles (e.g., ash; ASTM D-189) are preferably limited to≤2 parts per million weight (ppmw) on hydrocarbon feed, more preferably≤1 ppmw. Combustible non-volatiles (e.g., tar, asphaltenes, ASTM D-6560) may be present at concentrations below 5% of the hydrocarbon feed, preferably at concentrations below 1%, more preferably at concentrations below 100 ppmw, and most preferably at concentrations below 10 ppmw of the total feed to the reactor (e.g., first pyrolysis feed or second pyrolysis feed), as long as the presence of the combustible non-volatiles do not result in excessive (e.g., ≥2 or≥1 ppmw) concentrations of non-combustible non-volatiles. As a first example, the hydrocarbon feed may comprise crude oil and crude oil components, which may be separated into different feeds for the different reactors. As a second example, the pyrolysis feed for one of the reactors may comprise substantially methane (e.g., ≥50 wt %, ≥75 wt %, or≥90 wt % of the pyrolysis feed). Certain exemplary embodiments of this process are described further below in FIGS. 3 to 5.

Figure 3:
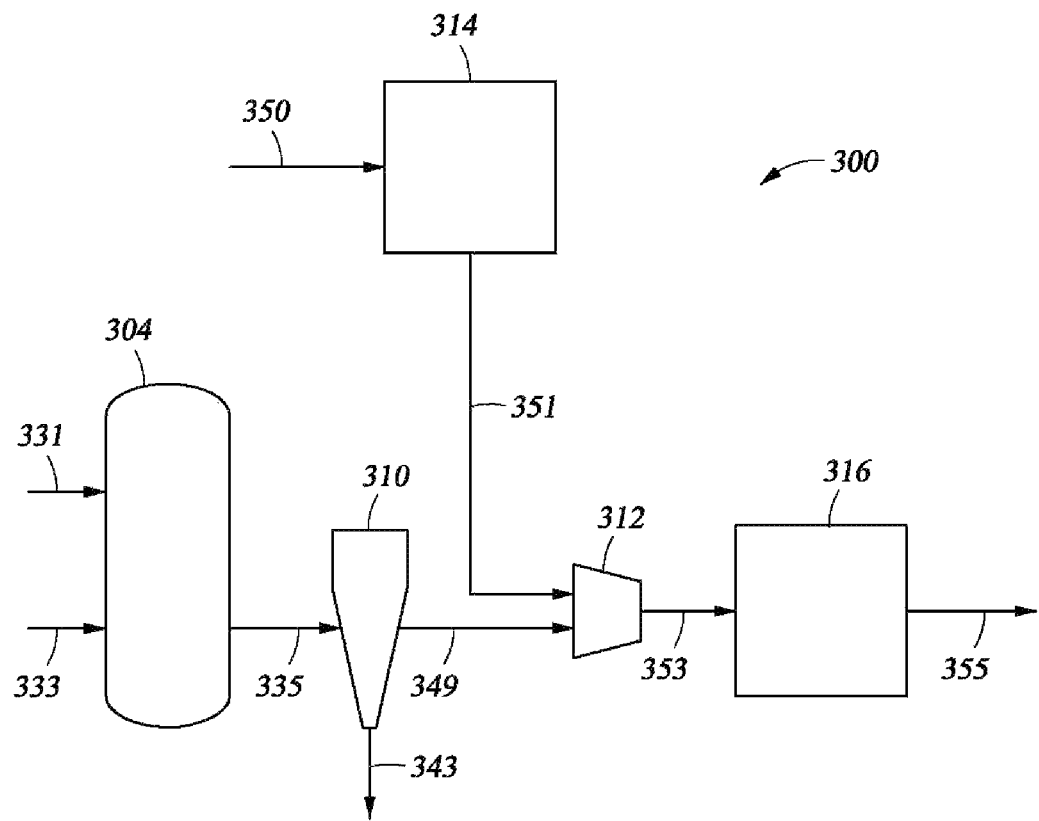
FIG. 3 is a simplified diagrammatic illustration of an exemplary process for converting a first pyrolysis feed and a second pyrolysis feed into conversion products in accordance with an embodiment of the present techniques.

FIG. 3 is a simplified diagrammatic illustration 300 of an exemplary process for converting first pyrolysis feed and a second pyrolysis feed into a conversion product in accordance with an embodiment of the present techniques. In this illustration 300, a particular configuration of unit operations (i.e. units) are coupled together to convert pyrolysis feeds into conversion products. These units may include a first pyrolysis reactor 304, a second pyrolysis reactor 314, tar/solid removal unit 310, a compressor 312, and a converter 316. In particular for this configuration, the cracking stage may include the first pyrolysis reactor 304, which is operated at high-severity operating conditions, and a second pyrolysis reactor 314, which is a different type of pyrolysis reactor from the first pyrolysis reactor. The recovery stage may include tar/solid removal unit 310, a compressor 312, and a converter 316. The process will now be explained in more detail.

A first pyrolysis feed, such as fuel oil (e.g., atmospheric resid) and/or natural gas, or blends thereof, is provided via line 331 to the first pyrolysis reactor 304. The first pyrolysis feed may be derived from a hydrocarbon feed that may have a hydrogen content of 6 wt % (weight percent) to 25 wt %, 8 wt % to 20 wt % (e.g., not methane), or 20 wt % to 25 wt % (e.g., natural gas). Optionally, a diluent feed may be provided via line 333, which may include $H_2$, water or a lighter hydrocarbon, which lighter hydrocarbon is preferably a hydrocarbon with a high hydrogen content that the feed it is to be mixed with. Alternatively, the diluent feed may be an oxidant or combustion products for certain reactors, such as PDX reactors or indirect combustion reactors, respectively. The diluent feed may be used to adjust the hydrogen content of the combined feed above a certain threshold. The pyrolysis or combined feed may optionally be adjusted to have a hydrogen content within a predetermined range, as noted above.

The first pyrolysis reactor 304, as noted above, may include any high-severity pyrolysis reactor, or may preferably include a regenerative reverse flow reactor. Accordingly, the first pyrolysis reactor 304 may have different piping configurations to provide combustion feed (e.g., fuel) and the first pyrolysis feed separately, depending on the specific configuration.

The first reactor effluent or reactor product from the first pyrolysis reactor 304 is conducted away via line 335 to the solid removal unit 310 and other recovery stage units. The solid removal unit 310 may include water scrubbing, oil scrubbing, cyclone separation, electrostatic separation, filtration, and/or moving bed adsorption. As may be appreciated, each of these systems may be combined together in one or more units to overcome certain limitations within the system. For instance, water scrubbing is effective to remove solid carbon black and other solids, but it limits the recovery of heat in the effluent. Oil scrubbing may be utilized for heat recovery, but it may present problems with fouling and emulsion formation. Cyclone separation may be limited to remove solid carbon, but not other smaller or fine solids. Electrostatic separation may have problems with clogging and short-circuiting due to carbon deposit buildup. Adsorption and filtration are limited to handling small amounts of solids and may be problematic for larger amounts of solids. As a result, one or more of these techniques may be coupled together in series to provide the separation. The solid-liquid phase of the at least a portion of the reactor product may be conducted away from solid removal unit 310 as a bottoms product, which may be a bottoms stream, via line 343. The bottoms product may include carbon black, soots, and/or heavy aromatic oils and/or tars. If the bottoms product is "dry", it may be handled via filtration or electrostatic separation; if sticky or wet, it may be better handled via washing (oil or water) or absorption. The bottoms product may be recycled to the first pyrolysis reactor, may be recycled to the second pyrolysis reactor or may be used as a fuel (in the first pyrolysis reactor and/or second pyrolysis reactor). The remaining portion of the reactor effluent or reactor product may be withdrawn from solid removal unit 310 as an overhead stream via line 349 and passed to the compressor 312.

A second pyrolysis feed, such as naphtha and/or other suitable feed, is provided via line 350 to the second pyrolysis reactor 314. The second pyrolysis feed may be derived from a hydrocarbon feed that may have a hydrogen content of 6 wt % to 25 wt %, 8 wt % to 20 wt % (e.g., not methane), or 20 wt % to 25 wt % (e.g., natural gas). Optionally, a diluent feed may be provided via line (not shown), which may include $H_2$, water or a lighter hydrocarbon, which lighter hydrocarbon is preferably a hydrocarbon with a high hydrogen content. Alternatively, the diluent feed may be an oxidant or combustion products for certain reactors, such as PDX reactors or indirect combustion reactors, respectively. The diluent feed may be used to adjust the hydrogen content of the combined feed above a certain threshold. The combined or pyrolysis feed may optionally be adjusted to have a hydrogen content within a predetermined range, as noted above.

The second pyrolysis reactor 314, as noted above, may include a high-severity pyrolysis reactor, which is not of the same type as the first pyrolysis reactor, or any low-severity reactor. Accordingly, the second pyrolysis reactor 314 may have different piping configurations to provide combustion feed (e.g., fuel) and the second pyrolysis feed separately, depending on the specific configuration. The second reactor effluent or reactor product from the second pyrolysis reactor 314 is conducted away via line 351 to the compressor 312, and/or other recovery stage units. For instance, a tar/solids removal unit (not shown) may be in fluid communication between the second pyrolysis reactor 314 and the compressor 312. At least a portion of the first reactor product and at least a portion of the second reactor product may be combined in a combining unit (not shown), such as a manifold, line joint (e.g., within lines 349 and 351), or within a mixing region prior to the compressor or as part of the compressor 312.

The compressor 312 may receive the vapor product from the solid removal unit 310, which is the remaining portion of the first reactor product, along with the second reactor product and compress the remaining reactor products. The compressed reactor products may be provided via line 353 to the converter 316. The compressor 308 may compress one or more of the remaining reactor products to a pressure from 50 psig (345 kPag) to 400 psig (2758 kPag), or from 150 psig (1034 kPag) to 300 psig (2068 kPag). For other embodiments, the pressure may be adjusted for hydrogen ($H_2$) removal (e.g., pressure swing adsorption, hydrogen membrane and/or cryogenic distillation, electrochemical separation) and acetylene hydrogenation.

Optionally, the converter 316 may receive the remaining reactor product (e.g., $C_2U$ stream or products comprising acetylene and ethylene) from the separation unit 310. The converter may include different units depending on the desired conversion product, such as an acetylene converter or propylene converter. If the converter 316 is an acetylene converter (A/C), it selectively hydrogenates the acetylene to ethylene without significantly hydrogenating the ethylene to ethane. The acetylene converter may operate at feed levels ranging from 0.5 to 15 mol % acetylene. The acetylene converter may operate at pressures from 32 psig (221 kPag) to 400 psig (2758 kPag), at inlet temperatures of 50° C. to 300° C. and may utilize catalyst comprising group VI or VIII catalysts. Conversion levels for the hydrotreater may range from 70 wt % to 100 wt % acetylene conversion and may have selectivity to ethylene from 70 wt % to as high as 98 wt % to ethylene. The acetylene converter may include an optional finishing acetylene converter to convert remaining levels of acetylene at 100 wt % conversion of the acetylene.

This finishing acetylene converter may be in fluid communication with the one or more units, such as the acetylene converter or other units downstream of the converter 316. The acetylene converter may include a hydrogenation unit, and optionally may further include a compressor, stream recycle components, desorption unit and/or separation unit.

The conversion product may be passed to a purification unit (not shown) via line 355, which may include a demethanator tower (to remove $H_2$, $CH_4$, $N_2$ and CO) and a $C_2$ splitter to remove ethane and upgrade ethylene to polymer grade ethylene. The purification unit may also include $C_2$ or $C_3$ refrigeration train, compression and additional distillation towers. This purification unit may separate the conversion product from the acetylene converter into one or more products and an upgraded product, such as an ethylene stream. The one or more products may include different light gas products (e.g., hydrogen, carbon monoxide, nitrogen, methane, and the like) or heavier products (e.g., ethane and $C_3^+$ streams). A portion of the recovered products may be recycled for processing again in the first pyrolysis reactor or second pyrolysis reactor, such as methane and/or hydrogen. Further, if the upgraded product is an ethylene stream, it may be provided to the ethylene polymerization unit.

Further, an optional ethylene polymerization unit may be a catalytic reactor, which may include a gas catalyst and/or a liquid catalyst. The process may involve a catalyst, solvent and the feed stream, as discussed above. Further, in some embodiments, a portion of the acetylene in the reactor product may optionally be combined with other process steps to form other products. In particular, the portion of the acetylene may be an intermediate product or precursor in a process within a chemical plant, in route to other preferred products, such as vinyl esters, ethylene, acetaldehyde, propanal, propanol, acrylic acid, and/or the like.

In one or more embodiments, different products, such as different light gases or heavier products may be separated from the remaining portions of the first reactor product, the second reactor product, or combined reactor products in one or more separation units. The separation processes may include the different units discussed above along with caustic wash, amine scrubber and/or other treatments, which may also include steps to remove different products (e.g., $CO_2$, $H_2S$ and/or $H_2O$) from the process. For instance, carbon dioxide can be removed by washing the reactor product. This step may also include drying to remove entrained water. The remaining reactor products may be recovered from the separation unit and passed to the converter 316, while the impurities may be withdrawn as products or bottom streams, which may be further processed for the different impurities.

Figure 4:
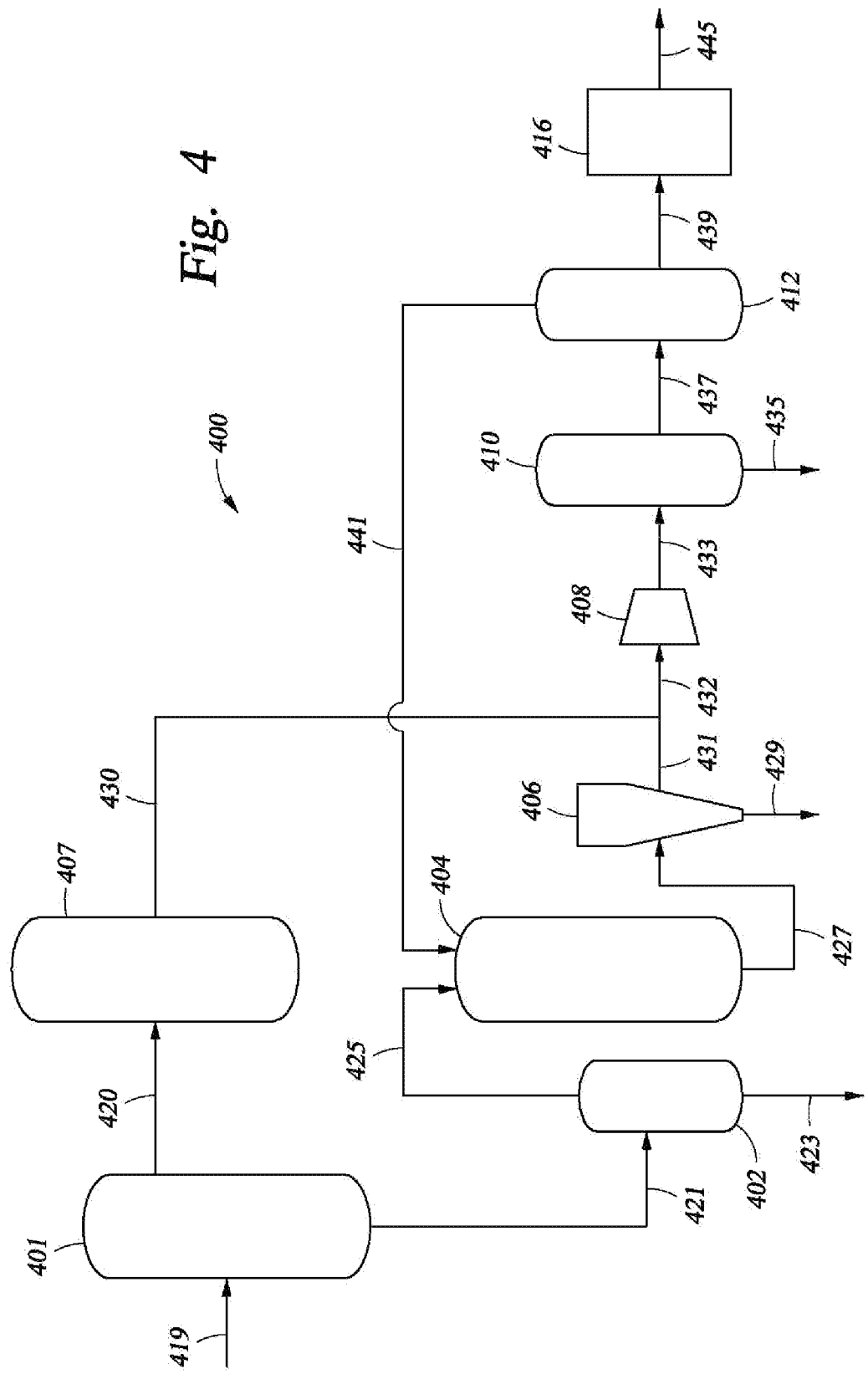
FIG. 4 is a simplified diagrammatic illustration of another exemplary process for convert hydrocarbon feed into conversion products in accordance with an embodiment of the present techniques.

FIG. 4 is a simplified diagrammatic illustration 400 of an exemplary process for converting hydrocarbon feed into a conversion product, such as ethylene, and optionally polyethylene, in accordance with an embodiment of the present techniques. In this illustration 400, a particular configuration of units are coupled together to convert a hydrocarbon feed to conversion products. These units may include a separation unit 401 and 402, a first pyrolysis reactor 404, a second pyrolysis reactor 407, a solid removal unit 406, a compressor 408, a separation unit 410, a converter 412, an upgrading unit 416. In particular for this configuration, the feed preparation stage may include the separation unit 401 and 402, the cracking stage may include the first pyrolysis reactor 404 and second pyrolysis reactor 407, and the recovery stage may include solid removal unit 406, a compressor 408, a separation unit 410, a converter 412 and an upgrading unit 416. The process will now be explained in more detail.

A hydrocarbon feed is provided via line 419 to the feed separation unit 401. The hydrocarbon feed may be crude oil, a fraction of crude oil components or other suitable hydrocarbons. The feed separation unit 401 may divide the hydrocarbon feed into two or more products, such as a first hydrocarbon feed and a second hydrocarbon feed, which may be the second pyrolysis feed. The feed separation unit 401 may be a flash drum separator, an atmospheric distillation column, or a fractionator.

The first hydrocarbon feed, such as fuel oil (e.g., atmospheric resid) and/or natural gas, or other suitable hydrocarbon feed, is provided via line 421 to the separation unit 402. As noted above, the first hydrocarbon feed may have a hydrogen content within a specific range, as noted above. Optionally, similar to the discussion above, a diluent feed may be provided via line (not shown) to adjust the hydrogen content. The diluent feed may comprise hydrogen, light hydrocarbon, light gas recycle or other diluents and the diluent to feed weight ratio may be used to adjust hydrogen content and/or the vapor liquid equilibria. The separation unit 402 may be used to separate the first hydrocarbon feed into a vapor product and a bottoms product (e.g., solid/liquid product). Examples of equipment suitable for separating the vapor product from the bottoms product include a knockout drum (e.g., substantially any vapor-liquid separator), a flash drum, distillation column/unit, flash drum having a heating means within the drum, a knockout drum having heating means within the knock-out drum, and combinations thereof. During separation the temperature of the separation unit 402 is maintained between 50° C. and 750° C. or preferably between 100° C. and 515° C., which may be adjusted to control the separation level within the separation unit 402. Depending on the first hydrocarbon feed, the vapor product (e.g., the first pyrolysis feed) may be readily separated from the remaining non-volatiles. Without separation, the bottoms product of the first hydrocarbon feed may foul downstream lines or units. The bottoms product, which may include non-volatiles, may be withdrawn or removed from the separation unit 402 as a bottoms product via line 423, which may be further processed or utilized for fuel for the first pyrolysis reactor 404 or other units. The vapor product, which may be the first pyrolysis feed or reactor feed if a diluent is later added to it, may be withdrawn from separation unit 402 as an overhead stream via line 425 and passed to the first pyrolysis reactor 404. The first pyrolysis feed may optionally be adjusted to have a hydrogen content within a predetermined range, as noted above.

The first pyrolysis reactor 404, as noted above, may include any high-severity pyrolysis reactor, or may preferably be a regenerative reverse flow reactor. Accordingly, the first pyrolysis reactor 404 may have different piping configurations to provide combustion feed (e.g., fuel) and the first pyrolysis feed separately, depending on the specific configuration.

The first reactor effluent or reactor product from the first pyrolysis reactor 404 is conducted away via line 427 to the solid removal unit 406 and other recovery stage units. The solid removal unit 406 may include water scrubbing, oil scrubbing, cyclone separation, electrostatic separation, filtration, and/or moving bed adsorption. As may be appreciated, each of these systems may be combined together in one or more units to overcome certain limitations within the system. For instance, water scrubbing is effective to remove solid carbon black and other solids, but it limits the recovery of heat in the effluent. Oil scrubbing may be utilized for heat recovery, but it may present problems with fouling and emulsion formation. Cyclone separation may be limited to remove solid carbon, but not other smaller or fine solids. Electrostatic separation may have problems with clogging and short-circuiting-due to carbon deposit buildup. Adsorption and filtration are limited to handling small amounts of solids and may be problematic for larger amounts of solids. As a result, one or more of these techniques may be coupled together in series to provide the separation. The solid-liquid phase of the first reactor product may be conducted away from solid removal unit 406 as a bottoms product, which may be a bottoms stream, via line 429. The bottoms product may include carbon black, soots, and/or heavy aromatic oils and/or tars. If the bottoms product is "dry", it may be handled via filtration or electrostatic separation; if sticky or wet, it may be better handled via washing (oil or water) or absorption. The remaining portion of the reactor effluent or reactor product may be withdrawn from solid removal unit 406 as an overhead stream via line 431 and passed to the compressor 408, which may operate similar to the compressor 306 of FIG. 3.

The second pyrolysis feed, derived from or comprising at least a portion of the second hydrocarbon feed from the feed separation unit 401, such as naphtha or other suitable portion of the hydrocarbon feed, is provided via line 420 to the second pyrolysis reactor 407. As noted above, the second pyrolysis feed may have a hydrogen content within a specific range, as noted above. Optionally, similar to the discussion above, a diluent feed may be provided via line (not shown) to adjust the hydrogen content. The second pyrolysis reactor 407, as noted above, may include any other high-severity pyrolysis reactor type or any low-severity reactor, as noted above. The second pyrolysis reactor 407 may have different piping configurations to provide combustion feed (e.g., fuel) and the second pyrolysis feed separately, depending on the specific configuration.

At least a portion of the second reactor product may be passed via line 430 to be combined with remaining portion of the first reactor product provided via line 431 into a combined reactor product via line 432. These remaining reactor products may be combined together in a combining unit, such as manifold, piping, a mixer or specific unit, similar to the discussion above. Then, the combined reactor products may be compressed in the compressor 408. The compressor 408 may operate similar to the compressor 308 of FIG. 3. Then, different products, such as different light gases or heavier products may be separated from the remaining reactor product in the separation unit 410. The separation unit 410 may include the different units discussed above along with caustic wash, amine scrubber and/or other treatments, which may also include steps to remove different products (e.g., $CO_2$, $H_2S$ and/or $H_2O$) from the process. For instance, carbon dioxide can be removed by washing the reactor product. This step may also include drying to remove entrained water. The remaining reactor product may be recovered from the separation unit 410 as via line 437 and passed to the converter 412, while the impurities may be withdrawn as products or bottom streams via line 435, which may be further processed for the different impurities.

Optionally, the converter 412 may receive the remaining reactor product (e.g., $C_2U$ steam or products comprising acetylene and ethylene) from the separation unit 410. The converter 412 may include a propylene converter or an acetylene converter, as noted above in FIG. 3, and convert the at least portion of the reactor product into a conversion product. The converter 412 may include separation units that separate a recycle product, which may include unreacted components or other products. The recycle product may be provided to the first pyrolysis reactor 404 via line 441 to be combined with the first pyrolysis feed or as combustion feed.

Optionally, the upgrading unit 416 may be used to process the conversion product provided via line 439 into a final product, such as polyethylene or polypropylene. If the conversion product is an ethylene stream, it may be converted in an ethylene polymerization unit. This unit may be a catalytic reactor, which may include a gas catalyst and/or a liquid catalyst. The process may involve a catalyst, solvent and the feed stream, as discussed above. Further, in some embodiments, a portion of the acetylene in the reactor product may optionally be combined with other process steps to form other products. In particular, the portion of the acetylene may be an intermediate product or precursor in a process within a chemical plant, in route to other preferred products, such as vinyl esters, ethylene, acetaldehyde, propanal, propanol, acrylic acid, and/or the like.

Beneficially, the separation of the different pyrolysis feeds from the hydrocarbon feed may be based on the different types of pyrolysis reactors. That is, the different types of pyrolysis reactors may be used to manage specific portions of the hydrocarbon feed. As such, this configuration is able to receive a hydrocarbon feed and process specific components in a second pyrolysis reactor and the advantaged portions of the feeds (e.g., methane) in the first pyrolysis reactor, which results in an efficient conversion of olefins. For example, methane, as noted in the examples above or natural gas, which may contain methane, ethane, propane and other natural gas liquids, such as butanes or condensates, may be provided to a high-severity reactor. Ethane and propane are typically cracked in steam crackers may be provided to a low-severity reactor. As another example, natural gas may be separated into methane and $C_2^+$ fractions (e.g., ethane and heavier saturates). The $C_2^+$ fraction or ethane rich fraction is preferentially cracked in an ethane steam cracker (e.g., as the second pyrolysis reactor) at conditions to yield high levels of ethylene, such as≥30 wt % of the reactor product. The steam cracker may include a recovery stage, which may include one or more heat exchangers (e.g., transfer line exchangers) or direct quench units, tar/solids removal units, compressors, separation units, acetylene conversion units and purification or upgrading units. The methane may be preferentially cracked in the high-severity pyrolysis reactor to yield a first reactor product comprising acetylene and ethylene. The first reactor may be in fluid communication with additional processing steps, such as tar/solids removal processes, compression or acetylene conversion, or may be processed or integrated with the existing steam cracker recovery steps. Similar for crude fractions, crude may be separated into methane, naphtha, distillates and aromatic gas oils. Naphtha and distillates are preferentially cracked in a liquid steam cracker (e.g., as the second pyrolysis reactor) at conditions to yield high levels of ethylene. The steam cracker may include a recovery stage that comprises the units noted above. However, the aromatic gas oils may be preferentially cracked in the high severity pyrolysis reactor to yield a first reactor product comprising acetylene and ethylene. The first reactor may be in fluid communication with additional processing steps, such as tar/solids removal, compression or acetylene conversion, or may be processed or integrated with the existing liquid steam cracker recovery steps.

As a further example, the different pyrolysis reactors may process feeds having different compositions. For instance, the first pyrolysis feed may have a first composition having a hydrogen content of the hydrocarbons in the first pyrolysis feed from 6 wt % to 12 wt % (e.g., aromatic gas oils) or from 20 wt % to 25 wt % (e.g., natural gas and/or methane) and the second pyrolysis feed has a second composition having a hydrogen content of the hydrocarbons in the second pyrolysis feed from 12 wt % to 20 wt % (e.g., ethane, light saturates and distillates). Accordingly, different compositions may be envisioned for the different reactors, which may be based on the reactor type and/or economics.

Figure 5:
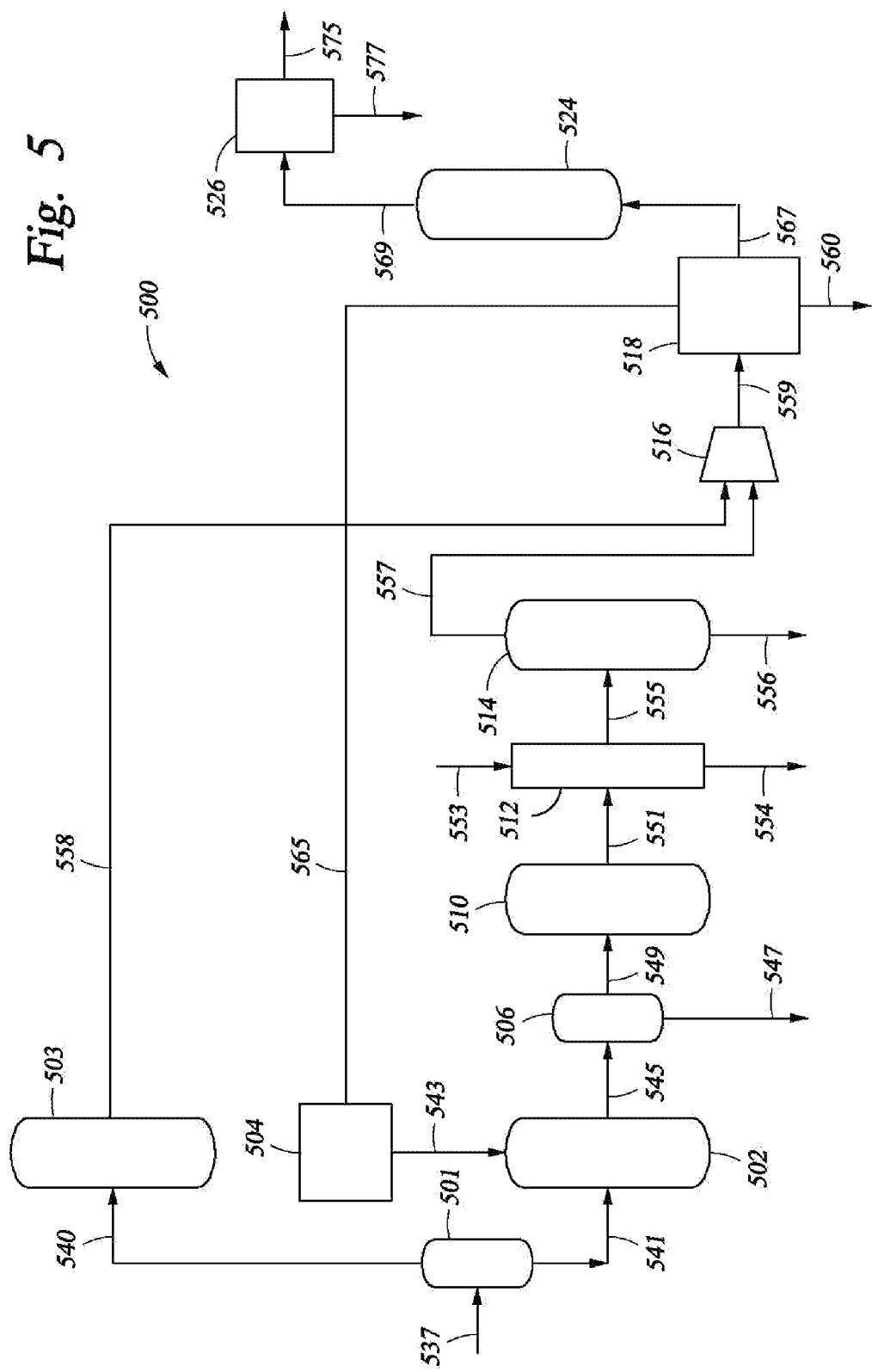
FIG. 5 is a simplified diagrammatic illustration of still yet another exemplary process for convert hydrocarbon feed to conversion products in accordance with an embodiment of the present techniques.

FIG. 5 is a simplified diagrammatic illustration of another exemplary process for converting a hydrocarbon feed into conversion products in accordance with an embodiment of the present techniques. In this process, hydrotreating may be utilized to treat the hydrocarbon feed being provided to the first pyrolysis reactor 510. The feed preparation stage may include a first separation unit 501, a hydrotreater 502, a gas heater 504 and a second separation unit 506, while the cracking stage may include the first pyrolysis reactor 510 and a second pyrolysis reactor 503. The recovery stage may include a heat exchanger 512, a solids removal unit 514, a compressor 516, a third separation unit 518, a converter 524 and an upgrading unit 526. In addition, a power conversion stage may also be utilized along with a polyethylene polymerization stage. Again, similar to the discussion related to FIGS. 2, 3 and 4, various units in this configuration may operate and function in a substantially similar manner to the units noted above in FIGS. 2, 3 and 4.

To begin, a hydrocarbon feed may be provided via line 537 to the first separation unit 501, which may be similar to the separation unit 401. From the first separator unit, a first hydrocarbon feed may be provided via line 541 to a hydrotreater 502 and a second hydrocarbon feed, which may be the second pyrolysis feed, may be provided via line 540 to the second pyrolysis reactor 503. The first hydrocarbon feed may include resid, such as crude, atmospheric resid, vacuum resid, and/or other streams containing asphaltenes, for example. Along with the first hydrocarbon feed, a dilution feed may be provided to the hydrotreater 502 via line 543. The diluent feed may include steam, methane, hydrogen or any combination thereof.

The hydrotreater 502 may be a high-severity hydrotreater. This hydrotreater 502 may be configured to add hydrogen to break up heavy molecules, which includes using hydrogen to separate aromatic cores from each other without saturating the aromatic cores (e.g., hydro visbreaking). The hydrotreating unit may operate at low hydrogen partial pressure to avoid hydrogen incorporation or aromatic saturation. The hydrotreating unit may operate at pressures between 200 psig and 2000 psig (between 1379 kPag and 13789 kPag) and at space velocities (LHSV) from 0.1 to ≥20. Hydrogen consumption for the hydrotreating process may be as low as 200 standard cubic feed per barrel (scf/bbl) and as high as 2000 scf/bbl at higher hydrogen pressures. The hydrotreating processes may involve combining the hydrocarbon feed containing resid with a hydrogen containing stream, which may be a separate stream or a recycle product (e.g., hydrogen product) from the recovery stage. Preferably, the hydrotreating process converts the non-volatile components to lighter volatile hydrocarbons. Resid conversion (e.g., conversion of non volatiles that boil above 565° C.) may be ≥20 wt %, ≥40 wt %, ≥50 wt %, ≥60 wt % or ≥80 wt %. The hydrotreating process may also convert aromatic carbon to aliphatic carbon. Preferably, aromatic carbon conversion is less than the amount of the non-volatile conversion. Hydrotreating or hydrovisbreaking is preferred over visbreaking because hydrotreating increases resid conversion and reduces downgrading heavier components. Aromatic carbon conversion may be ≤10 wt %, ≤20 wt %, ≤30 wt % or ≤50 wt %. In some embodiments of the present invention, the extent of aromatic carbon conversion may be less than half of the extent of resid, less than one-fourth of the extent of resid conversion or less than one-sixteenth of the extent of resid conversion.

After hydrotreating, the hydrotreated product is provided from the hydrotreater 502 via line 545 to the second separation unit 506. The separation unit 506 may be a flash drum or other suitable separation device, similar to the separation units above. The second separation unit 506 may divide the hydrotreated product into a feed for the first pyrolysis reactor, which may be the first pyrolysis feed, and a bottoms product. The bottom product may include the non-volatiles. The bottom product may be further passed for further processing via line 547.

The first pyrolysis feed may then be provided to the first pyrolysis reactor 510 via line 549. Similar to the discussion above, the first pyrolysis reactor 510 may include any of the high-severity pyrolysis reactors, which may preferably be a thermal pyrolysis reactor (e.g., a reverse flow regenerative reactor). Once cracked, the first reactor product from the first pyrolysis reactor 510 may be further processed in the recovery stage, in a similar manner to the discussion above for FIGS. 3 and 4. Initially, at least a portion of the first reactor product may be passed to the heat exchanger 512 via line 551. The heat exchanger 512 may cool the first reactor product from the reactor sufficiently for compression. The cooled reactor product may then be provided to a solids removal unit 514 via line 555, which may include an oil wash unit, for example. From the solids removal unit 514, a bottoms product comprising solids and/or tars may be provided via line 556 for further processing.

The second pyrolysis feed may be cracked in the second pyrolysis reactor 503 via line 540. Similar to the discussion above, the second pyrolysis reactor 503 may include any of the other high-severity pyrolysis reactors or low-severity pyrolysis reactors, which is a different type from the first pyrolysis reactor. Once cracked, at least a portion of the second reactor product from the second pyrolysis reactor 503 may be further processed in the recovery stage, in a similar manner to the discussion above for FIGS. 2, 3 and 4.

At least a portion of the first reactor product via line 557 and at least a portion of the second reactor product via line 558 may be combined in a variety of different manners, as noted above, in a combining unit. The respective reactor products may then be provided to a compressor 516. The compressor 516, which may operate similar to the compressors noted above. The pressurized stream may then be provided via line 559 to the third separation unit 518. The third separation unit 518 may separate light gas products and heavier products. The third separation unit 518 may include a hydrogen separation unit to separate the recycle product, such as hydrogen, from the remaining reactor product. The recycle product may be provided via line 565 to a gas heater 504 or may be utilized in other units (not shown). For example, the light gas product may be used as component of the first or second pyrolysis feed, as a combustion fuel, as hydrotreating feed, a stripping agent or a product. The remaining reactor product may be passed via line 567 to the converter 524, which may operate similar to the converters discussed above. The bottoms product may be passed via line 560 for further processing in other units (not shown). The remaining reactor product may be processed in the converter 524 and the conversion product may be provided via line 569 to the upgrading unit 526, which may operate similar to the purification and upgrading units noted above. As a result of the upgrading process, the conversion product, such an ethylene stream, which may be provided via line 575, may be provided to the other units for further processing, such as an ethylene polymerization unit (not shown).

This configuration may be utilized to further enhance the processing of a hydrocarbon feed by dividing the hydrocarbon feed into a first portion (e.g., an advantaged feed portion) that is processed and provided to the first pyrolysis reactor and a second portion (e.g., the second pyrolysis feed) provided to the second pyrolysis reactor. That is, the first hydrocarbon feed may have higher boiling point fuel oils, which are converted into a lower average molecule weight stream. For instance, the process takes a lower value feed having a higher average boiling curve and converts this into chemical products, such as ethylene, instead of using these feeds as fuel. As a result, combustible non-volatiles may be converted into volatiles and thereby utilized as a hydrocarbon feed for this process.

Although the units of FIGS. 2 to 5 are shown as respective single and separate units, each of these units can alternatively comprise a plurality of units. For example, a separation unit may include more than one knockout drums, separators, and/or flash drums. Accordingly, different embodiments may utilize different units in this manner. Further, some additional embodiments, which are discussed further below, may be utilized in these embodiments of FIGS. 2 to 5.

In certain embodiments, the pyrolysis reactor may be operated at different pressures to further enhance the operation of the system. For example, in some embodiments, the pyrolysis of volatized hydrocarbons may occur at different pressures, such pressures≥4 psig (28 kPag), ≥36 psig (248 kPag), ≥44 psig (303 kPag) or≥103 psig (710 kPag), but the pressures may be≤300 psig (2068 kPag), ≤163 psig (1124 kPag), or≤150 psig (1034 kPag), or different combinations thereof. Pressures higher or lower than that disclosed above may be used, although they may be less efficient. Further, for a regenerative reverse flow reactor, the pressure in the pyrolysis step may be similar or different to the pressure in the combustion step (e.g., at lower or higher pressure than the pyrolysis step).

Each of the pyrolysis reactors may be operated at different temperatures based on the specific operation and process variations. The different pyrolysis reactors may include specific mechanisms and processes to heat the pyrolysis feeds. As such, each pyrolysis reactor and/or separation unit may include different means for measuring the temperature of that specific process.

Accordingly, in one or more of the embodiments, a control mechanism may be utilized to manage the separation of the hydrocarbon feed into the different pyrolysis feeds. The control mechanism may include a process control unit coupled to one or more measurement devices that measure operational data (e.g., temperature, hydrogen content, composition, pressure, and the like) and one or more control units for adjusting operational settings (e.g., amount fuel provided to the pyrolysis reactors, pressure for the different units or the like). The process control unit, measurement devices and/or control units may communicate with each other via a physical and/or wireless means.

The process control unit may include a computer system along with one or more monitors and input/output components. The computer system may include memory to store sets of instructions and operational data and a processor to execute the instructions and access the operational data. In this system, operational settings may be adjusted to manage or refine the processing of the feeds within the system and to manage the operating parameters. For instance, operational settings may be adjusted in the system to further refine the separation of the hydrocarbon feed into products or feeds, such as the first pyrolysis feed and the second pyrolysis feed. These operating parameters may include monitored values, which are stored as operational data in the memory, and utilized by the processor in executing one or more sets of instructions to monitor the flow of hydrocarbons through the system, to adjust operational settings, and other similar operations.

Along with the process control unit, the control mechanism may include different types of measurement devices, such as a temperature measurement device and/or a hydrogen measurement device. The temperature measurement device, which may include a thermocouple, may be configured to measure the temperature of the hydrocarbon feed prior to the separation unit, the temperature of the products from the separation unit, temperature of the pyrolysis feeds prior to the respective pyrolysis reactor. The hydrogen measurement device, which may include nuclear magnetic resonance spectrometer (NMR), gas chromatograph (GC) or specific gravity/boiling curve analyzer and may be configured to measure the hydrogen content of the feeds, such as the hydrocarbon feed, first pyrolysis feed, and second pyrolysis feed.

The one or more control units may include different control units to adjust different operational settings. For example, a dilution control unit may be utilized and configured to adjust the amount of a fluid mixed with the first pyrolysis feed or the second pyrolysis feed prior to being passed to the respective pyrolysis reactor and/or the hydrocarbon feed prior to the separation unit.

The present techniques may monitor certain operating parameters and adjust operational settings to provide an enhanced process. For instance, the control mechanism may include a hydrogen measurement device configured to measure hydrogen content of the first pyrolysis feed prior to the first pyrolysis reactor. The control mechanism may also include a process control unit having a set of instructions stored in memory and accessed via a processor, which are configured to (i) receive operational parameters from the hydrogen measurement device; (ii) to calculate the amount of diluent feed; and provide an indication to a diluent control unit to adjustment to the flow rate of the recycle stream based on the determined flow rate.

To provide the separation, operating parameters may be monitored and adjusted to vary the separation level. The operating parameters may include temperature of the hydrocarbon feed, pressures within different vessels along the flow path to the separator or within the separator. These operating parameters may be monitored, stored in memory as operational data, and utilized to adjust operational settings, which may be stored in memory, via a computer system. The determination of the separation level may be calculated by the computer system in the process control unit, prior to the hydrocarbon feed being provided to the separator, prior to offloading the feed, or prior to purchasing the hydrocarbon feed. Further, the determination of the separation level may be adjusted in real time or concurrently with the processing of the hydrocarbon feed, depending on the specific configuration.

Based on the operational data from these measuring devices, the computer system of the process control unit may calculate a separation level or access a previously determined separation level. A comparison of the operational data (e.g., flow rates for this example) and the desired separation level may be performed, which may be a difference comparison or other suitable comparison. Based on the comparison, the computer system of the process control unit may adjust the flow valves coupled along the lines to increase or decrease the flow. As another possible adjustment, if the separation unit is a manifold or other device with one or more valves for each of the light fraction streams and/or the heavy fraction streams, the control mechanism may adjust the different distillates being routed to the respective pyrolysis reactor. Accordingly, in this configuration, the flow rate may be used to manage the separation level.

As a specific example for a thermal pyrolysis reactor, the pyrolysis stream is heated by a solid material, which is heated by a combustion reaction. Usually, the solid material forms the channels that the pyrolysis stream travels through. The combustion reaction of combustion feed that heats the solid material may heat via convective and/or radiative mechanisms. In these reactors, the highest temperatures are observed in the stream that is heating the solids (e.g., combustion stream). At any location, the solid material has a temperature that is lower than that of the combustion stream from which it receives heat, while the pyrolysis stream being heated by the solid material has a temperature that is lower than the solid material. The specific temperature of the combustion stream, pyrolysis stream or solid material depends on its location within the reactor and on the configuration and/or operation of the pyrolysis reactor.

In certain thermal pyrolysis reactors (e.g., steam cracking furnace configuration), the heating and the pyrolysis process occur simultaneously, for example with a combusting stream on one side of partition (typically a wall or tubular) and the pyrolysis stream on the other side. Such reactors operate at or near steady state. The partition between the combustion feed and the pyrolysis feed has real physical dimensions and the temperature is not equal at every location. For example, on the combustion side, temperatures may be hottest near a flame region, and on the pyrolysis side temperatures increase with heat addition until some maximum temperature is reached. Steady state in these systems means that, at any given location relative to the fixed partition, temperatures remain relatively steady. However, the gases that travel through the reactor are heated and cooled by the chemistry and heat transfer that takes place in the reactor. The term "peak pyrolysis gas temperature" means the maximum temperature achieved by the bulk pyrolysis stream gases as they travel through the pyrolysis reactor (e.g., cracking region or radiant region). One skilled in the art will appreciate that temperatures immediately proximate to the partition may be higher, and may, in some infinitesimal layer, actually approach the solid temperature. However, the pyrolysis temperature referred to herein should be considered a bulk gas temperature, which is a temperature that could be measured by a device (such as a thermocouple) that is not in contact with the solid material. For example, if the gas is traveling through tubulars in a thermal pyrolysis reactor, the bulk gas temperature may be taken as the average temperature over any tubular cross-section, and the peak pyrolysis gas temperature as the highest cross-sectional-average temperature of the pyrolysis stream.

In a thermal pyrolysis regenerative reactor system, the heating and pyrolysis occur in sequential steps. First, a heating step, usually a combustion reaction or combustion step, is used to heat the solid material. Second, a pyrolysis step is carried out that absorbs heat from the solid material to effect a chemical reaction. The solid material may be in fixed orientation or in moving orientation. If moving, the solid is typically moved from a heating region to a pyrolysis region. Moving-solid systems appear to be step-wise from the perspective of the moving solid, however the gas streams may be at steady state in any absolute location, and temperatures are defined very much as discussed for thermal pyrolysis furnace-type reactors. When the solid material is in fixed orientation, a regenerative system may use valves to alternate introduction of pyrolysis and heating streams into the solid-containing region. The solid material may be designed to facilitate the process of heat addition and removal. Checker bricks, tiles and monoliths may be used as the solid materials within the reactor. Such materials form a network of passages that are used by the gases in each step to transit the region containing solid material. The heat addition step leaves a profile of temperatures in the solid material, that is, a temperature that varies along the path by which the gases transit the solid material. The shape of that profile depends on many factors, including if and where a heat release (combustion) reaction occurs, the initial temperature distribution, the duration of the heating step, the flow rate and inlet temperature of the gas stream, and the heat capacity and transfer properties of the gas and solid material. On average, the solid material is hottest at the end of the heating step. The pyrolysis step consumes heat and reduces average solid material temperature. The pyrolysis step changes the profile of temperatures in the solid material, in a way that depends on many factors, including where the heat consumption (pyrolysis) reaction occurs, the initial temperature distribution, the duration of the pyrolysis step, the flow rate and inlet temperature of the gas stream, and the heat capacity and transfer properties of the gas and solid. Fixed-solid regenerative pyrolysis reactors are not at steady state. That is, at any given location, the temperature changes. However, these reactors may be in a periodic steady state, meaning that the same cycling of temperatures occurs over and over as the reactor oscillates between heating and pyrolysis.

In a reverse-flow regenerative system, a reversal occurs in the direction of transit of the gases through the region that contains the solid material, and this reversal occurs in between the heating and pyrolysis steps. In some embodiments, reversal occurs between every step, and in other embodiments reversal occurs in alternating step changes. Regardless, the flow reversal enables substantial heat exchange between the incoming gas of one step and the outgoing gas of the alternate step. This results in a reactor that has highest temperatures near the middle of the flow path, and relatively cool temperatures at both ends of the reactor.

In a regenerative pyrolysis system, peak pyrolysis gas temperature is determined as follows. The peak pyrolysis gas temperature typically is experienced by the gases at the beginning of the pyrolysis step, because the solid material is typically at its highest temperature at the beginning of the pyrolysis step. One skilled in the art will appreciate that temperatures immediately proximate to the solid material may be higher, and may, in some infinitesimal layer, actually approach the solid temperature. However, the pyrolysis temperature referred to herein should be considered a bulk gas temperature, which is a temperature that may be measured by a device (such as a thermocouple) that is not in contact with the solid material. For example, if the gas is traveling through channels in a checker brick, tile or honeycomb solid material, the bulk gas temperature could be taken as the average temperature over any channel cross-section, and the peak pyrolysis gas temperature as the highest cross-sectional-average temperature of the pyrolysis stream.

Thermal pyrolysis reactors may also be characterized in terms of the residence time of pyrolysis gases in the reactor. Residence time is most generally defined as the time required for some average non-reacting molecule to pass through the pyrolysis reactor or furnace. Residence time may be further defined to be the time spent within the actively heated or cooled portions of the reactor or furnace. This includes time spent within tubulars or heat transfer solids of a furnace or regenerative reactor, respectively, but excludes residence time spent in headers or other means of conveyance to or from the actively heated or cooled regions of the furnace or reactor. Additionally, the high-severity residence time is defined as the time that pyrolysis stream components are exposed to temperatures above the severity threshold. An exact calculation of residence time requires measurements with tracer compounds (such as radioactive additives to the feed) or requires a specific knowledge of the temperature and composition of the pyrolysis stream at all times as it passes through the pyrolysis reactor. For the purposes of the present application, residence time (in either form) may be approximated using interpolation and extrapolation of discreet composition and temperature measurements, and/or using model-based estimations of temperature and composition, as is known in the art.

In addition to the operating pressure, the one or more embodiments may include the conversion of feedstocks into higher value hydrocarbons, such as acetylene, at different temperatures. These temperatures may include high temperature, which in the past has been a significant barrier to commercialization and efficiency. A high severity pyrolysis reactor according to the present techniques is a higher temperature hydrocarbon pyrolysis reactor that operates at higher temperatures than steam cracking reactors used in commercial steam cracking operations. For example, naphtha steam cracking operations typically operate at furnace radiant coil outlet temperatures of≤about 815° C., which corresponds to the peak pyrolysis gas temperature. However, the high severity thermal reactor may operate at peak pyrolysis gas temperatures between 1200.0° C. and 2200.0° C., preferably between 1400.0° C. to 1900.0° C. In particular, for reactors with an isothermal heat profile, the temperatures may be between 1450.0° C. and 1700.0° C., or between at least 1540.0° C. to 1650.0° C. For reactors with a Gaussian like heat profile, the peak pyrolysis gas temperatures may be between 1540.0° C. and 2200.0° C. or 1600.0° C. and 1800.0° C. In some reactions, it may even be still more preferable to expose a pyrolysis feed to heat using very short residence times, such as≤0.1 second, to a temperature in excess of 1600.0° C. Pyrolysis reactions that benefit from reaction or conversion of methane that may be a part of the pyrolysis feed, typically involve peak pyrolysis gas temperatures in excess of 1400.0° C. for the methane to react or convert. An exemplary preferred high severity thermal reactor may pyrolyze the feed stream within the reactor, such as at peak pyrolysis gas temperatures of from 1540.0° C. to 2200.0° C., and more preferably from 1600.0° C. to 1800.0° C. Exemplary residence times for that reactor preferably may be short, such as≤0.5 second, ≤0.3 second and preferably≤about 50 milliseconds or in the range of 0.5 seconds to 0.001 seconds. High severity residence times are preferably≤0.05 seconds, and more preferably≤0.02 seconds.

As described earlier, achieving any peak pyrolysis gas temperature for certain embodiments involves the existence of a solid temperature that is heated to a higher temperature, and a combustion gas temperature that is a higher temperature than the solid temperature. In one or more embodiments of the present techniques, the maximum temperature of the solid elements in a thermal pyrolysis system (e.g., tubulars for furnaces or heat transfer solids for regenerative systems) is between about 5° C. and about 500° C. higher than the peak pyrolysis gas temperature. In a preferred embodiment, the maximum temperature of the solid elements in a thermal pyrolysis system is between 10° C. and 100° C. higher than the peak pyrolysis gas temperature. Reverse flow regenerative thermal reactors may also include some amount of quenching by means of heat removal to the heat transfer solids. In reverse flow regenerative reactor embodiments of the present techniques, the pyrolysis gas may be cooled to a temperature between 100° C. and 1000° C. by means of heat removal to the heat transfer solids in the reactor, and more preferably cooled to a temperature between 300° C. and 550° C.

In one or more embodiments, the hydrocarbon feed may include different hydrocarbon components or mixtures thereof. For instance, the hydrocarbon feed may include methane, which may be part of a natural gas stream. This feed, including associated hydrocarbon and impurity gases, may be supplied into the reactor system. The supplied feed may be sweetened and/or dehydrated natural gas. Natural gas commonly includes various concentrations of associated gases, such as ethane and other alkanes, preferably in lesser concentrations than methane. The supplied natural gas may include impurities, such as hydrogen sulfide $H_2S$ and nitrogen. Certain embodiments may also serve to simultaneously convert some fraction of the associated higher hydrocarbons to acetylene. In other embodiments, the present techniques and compositions may be utilized with liquid feeds, such a vacuum gas oil (VGO) or naphthas.

In other embodiments, the first pyrolysis reactor may be a regenerative reverse flow reactor or regenerative pyrolysis reactor. As example, U.S. Ser. No. 61/226,499, which is incorporated by reference, describes a process and regenerative pyrolysis reactor utilized for pyrolyzing a resid-containing hydrocarbon feedstock. Further, other examples of such reactors may be found in U.S. Patent Application Publication Nos. 2007/0144940 and 2008/0142409. These references, which are incorporated by reference, teach a regenerative bed reverse flow reactor wherein the location of the exothermic reaction is controlled. The regenerative reactor bed is regenerated by supplying a first reactant through a first channel to a first regenerative bed and a second reactant through a second channel in the first regenerative bed, combining first and second reactants in a gas mixer, and reacting to produce a heated reaction product which is passed through a second regenerative bed to transfer heat thereto. Other examples may be found in U.S. Patent Application Publication No. 2007/0191664, 2009/0008292 and 2009/008292; U.S. Pat. No. 7,491,250; and U.S. patent application Ser. Nos. 61/349,464, 12/119,762, 12/121,353, which are each incorporated by reference.

As an example, U.S. Ser. No. 11/643,541 (U.S. Patent Application Publication No. 2007/0191664), which is incorporated by reference, describes a process and high severity regenerative thermal pyrolysis reactor utilized to manufacture acetylene from a methane or hydrocarbon-containing feed. These process steps and/or pyrolysis reactor may be utilized in one or more of the embodiments described above. For instance, the process may include a reactor system that includes (i) a first (quenching) reactor comprising a first end and a second end, and (ii) a second reactor comprising primary end and a secondary end, the first and second reactors oriented in a series relationship with respect to each other such that the secondary end of the second reactor is proximate the second end of the first reactor. The process may include a two-step process wherein heat is (1) added to the reactor media via in-situ combustion step and (2) removed from the reactor media via in-situ endothermic pyrolysis step. The combustion step may involve passing a first and second combustion reactant (combustion feeds) separately but simultaneously through the first (quenching) reactor, by supplying a first reactant through a first channel in the first reactor and supplying at least a second reactant through a second channel in the first reactor, such that the first and second reactants are supplied to the first reactor from the first end of the first reactor. The combustion step may further involve combining the first and second reactants at the second end of the first reactor and reacting the combined reactants to produce a heated reaction product; passing the heated reaction product through the second reactor to transfer at least a portion of the heat from the reaction product to the second reactor, and recovering an exhaust gas from the second reactor. Preferably, the combining is enhanced by a reactant (combustion feed) mixer that mixes the reactants to facilitate substantially complete combustion/reaction at the desired location, with the mixer preferably located between the first and second reactors. Thereafter, the endothermic pyrolysis step, which may be carried out at a pressure between about 5 pounds per square inch absolute (psia) (35 kPa absolute (kPaa)) up to about 45 psia (310 kPaa), supplies methane or other hydrocarbon through the heated second reactor to the first reactor, in flow direction the opposite to that of the heating (combustion) step, to convert at least a portion of the methane into acetylene; passing the supplied methane and the produced acetylene through the first reactor to quench the methane and the produced acetylene; and recovering the produced acetylene. The process may further include supplying hydrogen in the second reactor during the pyrolysis step to moderate the reaction of the methane or other hydrocarbons in the feed. Hydrogen may be used in molar ratio to methane of 0 to 5, preferably of 1 to 3 during the pyrolysis step. In a preferred embodiment, the media in the first reactor includes one or more honeycomb monolith structures that provide flow channels for the first and second reactant. The process may further include media of the first or second reactor that has wetted surface area between 50 and 3000 ft$^{-1}$, heat transfer coefficient ≥0.02 cal/cm$^3$s° C., and bulk heat capacity≥about 0.10 cal/cm$^{3°}$ C., and may be comprised of honeycomb monoliths having 40 to 80% open frontal area and between about 50 and 2000 channels per square inch. The process may further include compressors, blowers, or fans to supply air as one combustion feed during the combustion step, which may be carried out at a pressure between about 15 psia (103 kPaa) and 45 psia (310 kPaa); may include expansion turbines to recover mechanical energy from higher pressure exhaust gases; and may include recycle of exhaust gases (EGR) to the combustion feed for combination with the air, for example to reduce the oxygen content and the adiabatic flame temperature of the combustion feed. Noncombustible gases, for example $H_2O$, $CO_2$, and $N_2$, may be added to the combustion feed to reduce combustion temperature. The combustion step may comprise a first and second reactant that are a fuel gas and an oxidant that are maintained substantially separated as they pass through the first reactor and which combust or burn when combined. By substantially separated is meant that at least 50%, and more preferably 75% or 90% of the potential combustion that may occur after the axial transit of the first reactor. The process may further include a mixer that is comprised of multiple mixer segments, each preferably having similar cross-sectional area and length and each preferably accepting flow during the combustion step from roughly equal numbers of first and second channels, representing roughly equal proportions of first and second reactant, and having a characteristic L/D between 0.1 and 5.0. Preferably, the mixer has a total volume 20% of the total volume of mixer plus flow regions in first and second reactor, and preferably has a geometric void volume≤20% of the void volume in mixer plus first and second reactor. The process may further include a cycle time that includes the time spent in combustion step plus time spent in pyrolysis step plus any time needed to switch between steps. Typical cycle times may be between 1 and 240 seconds, or between 2 and 60 seconds, and without expectation that combustion and pyrolysis steps have equal durations.

In some other embodiments, the use of the materials may provide additional benefits in the selectivity of operations. For example, regenerative pyrolysis reactors have generally have not been used commercially to temperatures above 1300° C. because of the alumina internals and the process, as noted in the references discussed above. In a high severity regenerative thermal reactor, the operating temperatures within the reactor may reach temperatures up to 1500° C. to 2200° C. In this manner, such pyrolysis reactors materials have to be designed with withstand these temperature swings. That is, in the proposed configuration, pyrolysis reactors may have components or internals, such as valves, tubes, conductive monoliths, thin-walled honeycombs, bead-beds, mixers, quench media, and other reactor components, regardless of whether simple or complex shaped, that are directly associated with the pyrolysis reaction. These components made of different materials (e.g., substantially, predominately or partially made from a refractory material) may be able to withstand these larger temperature swings. As a specific example, U.S. Ser. Nos. 12/099,251; 12/277,056; 12/467,832; 12/772,757; and 12/623,046; which are each incorporated by reference, describe different material that may be used in a pyrolysis reactor.

The embodiments of the present techniques may also comprise different embodiments, such as in the following exemplary paragraphs:

1. A hydrocarbon conversion method comprising: exposing a first pyrolysis feed in a first pyrolysis reactor to a peak pyrolysis gas temperature≥1400.0° C. to produce a first reactor product comprising ethylene and acetylene, wherein the first pyrolysis feed has (i) a hydrogen content in the range of 6.0 wt % to 25.0 wt % based on the weight of hydrocarbon in the pyrolysis feed and/or (ii) a non-combustible, non-volatiles content<2.0 ppm based on the weight of the first pyrolysis feed; exposing a second pyrolysis feed to pyrolysis conditions in a second pyrolysis reactor to produce a second reactor product comprising ethylene and acetylene, wherein the first and second pyrolysis reactors are of different type and (i) the second pyrolysis feed has (i) a hydrogen content in the range of 6.0 wt % to 20.0 wt % based on based on the weight of hydrocarbon in the pyrolysis feed and/or (ii) a non-combustible, non-volatiles content≥2.0 ppm based on the weight of the second pyrolysis feed; and combining at least a portion of the first reactor product and at least a portion of the second reactor product to form a combined reactor product; wherein the first and second pyrolysis feeds comprise hydrocarbons, the hydrocarbons being derived from a hydrocarbon feed having a hydrogen content in the range of≤24.0 wt %.

2. A hydrocarbon conversion method comprising: exposing a first pyrolysis feed in a first pyrolysis reactor to peak pyrolysis gas temperatures≥1400.0° C. to produce a first reactor product; exposing a second pyrolysis feed in a second pyrolysis reactor to pyrolysis operating conditions produce a second reactor product, wherein the first pyrolysis reactor and the second pyrolysis reactor differ in one or more of (i) feed composition of the first pyrolysis feed as compared with the second pyrolysis feed, (ii) reactor product composition of the first reactor product compared to the second reactor product, or (iii) operating conditions in the first pyrolysis reactor as compared to the operating conditions of the second pyrolysis reactor.

3. The process of paragraph 2, comprising combining at least a portion of the first reactor product with at least a portion of the second reactor product to form a combined reactor product.

4. The method of paragraph 2 or 3, wherein the first pyrolysis feed comprises≥4.0 ppm of the non-combustible, non-volatiles based on the weight of the first pyrolysis feed.

5. The method of paragraph 4, wherein≥50.0 wt % of the first pyrolysis feed comprises hydrocarbon, the hydrocarbon having a hydrogen content in the range of from 6.0 wt % to 12.0 wt % and wherein≥50.0 wt % of the second pyrolysis feed comprises hydrocarbon, the hydrocarbon having a hydrogen content in the range of from 12.0 wt % to 20.0 wt %.

6. The method of any one of paragraphs 1 to 5, wherein the first reactor product has a $C_3^+$ to acetylene weight ratio≤0.45.

7. The method of any one of paragraphs 1 to 6, further comprising compressing the combined reactor product to form a compressed reactor product.

8. The method of any one of paragraphs 1 to 7, further comprising compressing at least one of (i) the at least a portion of the first reactor product or (ii) the at least a portion of the second reactor product prior forming the combined reactor product.

9. The method of any one of paragraphs 1 to 8, further comprising deriving the first pyrolysis feed and the second pyrolysis feed from at least one hydrocarbon feed.

10. The method of any one of paragraphs 1 to 9, wherein the peak pyrolysis gas temperature is≥1540.0° C.

11. The method of any one of paragraphs 1 and 3 to 10, further comprising converting at least a portion of the combined reactor product into a conversion product.

12. The method of paragraph 11, further comprising polymerizing at least a portion of the conversion product into one or more of polyethylene and polypropylene.

13. The method of any one of paragraphs 1 to 11, further comprising separating from the at least the first reactor product a bottoms product comprising tars and/or solids.

14. The method of any one of paragraphs 1 to 13, further comprising separating hydrogen from one or more of the at least a portion of the first reactor product, the at least a portion of the second reactor product and the combined reactor product.

15. The method of paragraph 11 or 12, further comprising separating hydrogen product from the conversion product.

16. The method of paragraph 14 or 15, wherein the hydrogen is separated via one or more of a hydrogen membrane, pressure swing adsorption, electrochemical, cryogenic separation, and solvent absorption.

17. The method of any one of paragraphs 14 to 16, further comprising combining at least a portion of the separated hydrogen with a combustion feed for one or more of the first pyrolysis reactor and the second pyrolysis reactor and reacting the combustion feed along with the at least a portion of the separated hydrogen to produce heat.

18. The method of any one of paragraphs 14 to 16, further comprising deriving one or more of the first pyrolysis feed and the second pyrolysis feed from at least a portion of the separated hydrogen.

19. The method of any one of paragraphs 14 to 16, further comprising combining a combustion feed with a first portion of the separated hydrogen from one or more of the first pyrolysis reactor and the second pyrolysis reactor and reacting the combustion feed along with the at least a portion of the separated hydrogen and comprising deriving one or more of the first pyrolysis feed and the second pyrolysis feed from a second portion of the separated hydrogen.

20. The method of any one of paragraphs 14 to 16 further comprising combining at least a portion of the separated hydrogen with the combined reactor product, the mixture being provided to an acetylene converter unit utilized to convert at least a portion of the mixture to an ethylene product.

21. The method of any one of paragraphs 1 to 20, wherein the peak pyrolysis gas temperature is in the range of 1540.0° C. to 2200.0° C., and wherein the exposing is for a residence time in the range from 0.5 second to 0.001 second.

22. The method of any one of paragraphs 1 to 20, wherein the peak pyrolysis gas temperature is in the range of 1600.0° C. to 1800.0° C., and wherein the exposing is for a residence time in the range from 0.5 second to 0.001 second.

23. The method of paragraph 1, further comprising: exothermically reacting a first combustion feed with a second combustion feed to heat a region at least partially within the first pyrolysis reactor; removing combustion products from the first pyrolysis reactor; and heating the first pyrolysis feed using at least a portion of the heat generated by the exothermic reaction.

24. The method of paragraph 23, comprising purging the region with a vapor purge stream after the removing the combustion products and prior to passing the first pyrolysis feed into the region.

25. The method of any one of paragraphs 23 to 24, wherein the first combustion feed and the second combustion feed are separately heated within the first pyrolysis reactor prior to exothermically reacting in the region.

26. The method of any of paragraphs 1 to 25, wherein the hydrocarbon feed is derived from crude oil and/or crude oil components.

27. The method of paragraph 26, wherein the second pyrolysis feed comprises≥50.0 wt % of $C_2^+$ saturates of the hydrocarbons in the hydrocarbon feed and the first pyrolysis feed comprises≥10.0 wt % of the hydrocarbon feed, based on the weight of the hydrocarbon feed.

28. The method of any one of paragraphs 1 to 25, wherein the first pyrolysis feed comprises≥50.0 wt % methane.

29. The method of any one of paragraphs 1 to 25, wherein the first pyrolysis feed comprises≥80.0 wt % methane.

30. The method of any of paragraphs 1 to 29, wherein the first pyrolysis reactor is operated under one of partial oxidation conditions; arc conditions; and thermal pyrolysis conditions.

31. The method of any one of paragraphs 1 to 29, wherein the second pyrolysis reactor is operated under low-severity operating conditions.

32. The method of any one of paragraphs 1 to 29, wherein the first reactor product has an ethylene to acetylene weight ratio≥0.5.

33. The method of any one of paragraphs 1 to 25, wherein the first pyrolysis reactor comprises a regenerative reverse flow thermal pyrolysis reactor and the second pyrolysis reactor comprises a steam cracking thermal pyrolysis furnace.
34. An apparatus for processing hydrocarbons comprising: a first pyrolysis reactor configured to expose a first pyrolysis feed to high-severity operating conditions to produce a first reactor product comprising ethylene and acetylene, wherein the first pyrolysis feed has (i) a hydrogen content in the range of 6.0 wt % to 25.0 wt % based on the weight of hydrocarbon in the pyrolysis feed and/or (ii) a non-combustible, non-volatiles content<2.0 ppm based on the weight of the first pyrolysis feed; a second pyrolysis reactor configured to crack a second pyrolysis feed to produce a second reactor product comprising ethylene and acetylene, wherein the first and second pyrolysis reactors are of different type and the second pyrolysis feed has (i) a hydrogen content in the range of 6.0 wt % to 20.0 wt % based on based on the weight of hydrocarbon in the pyrolysis feed and/or (ii) a non-combustible, non-volatiles content≥2.0 ppm based on the weight of the second pyrolysis feed; and a combining unit in fluid communication with the first pyrolysis reactor and the second pyrolysis reactor and configured to combine at least a portion of the first reactor product and at least a portion of the second reactor product into a combined reactor product.
35. The apparatus of paragraph 34, further comprising a compressor in fluid communication with the combining unit, the compressor being configured to compress at least a portion of the combined reactor product.
36. The apparatus of paragraph 34, further comprising a separation unit in fluid communication with the first pyrolysis reactor, the separation unit being configured to separate a bottoms product comprising tars and/or solids from the at least a portion of the first reactor product.
37. The apparatus of paragraph 34, further comprising a converter in fluid communication with the combining unit, the converter being configured to convert at least a portion of the combined reactor product into a conversion product.
38. The apparatus of paragraph 37, further comprising a polymerization unit in fluid communication with the converter, the polymerization unit being configured to convert at least a portion of the conversion product into polyethylene.
39. The apparatus of any one of paragraphs 37 to 38, further comprising a separation unit in fluid communication with the converter, the separation unit being configured to separate a hydrogen product from one of the at least a portion of the first reactor product and the combined reactor product prior to the converter.
40. The apparatus of any one of paragraphs 37 to 38, further comprising a separation unit in fluid communication with the converter, the separation unit being configured to separate a hydrogen product from the conversion product.
41. The apparatus of any one of paragraphs 39 to 40, wherein at least one separation unit comprises one or more of a hydrogen membrane, a pressure swing adsorption unit, an electrochemical unit, a cryogenic separation unit and a solvent absorption unit.
42. The apparatus of any one of paragraphs 39 to 40, further comprising one or more lines providing fluid communication between the separation unit and the first pyrolysis reactor, at least one line being configured to provide a portion of the hydrogen product to a combustion feed being provided to the first pyrolysis reactor, wherein the first pyrolysis reactor is configured to react the portion of the hydrogen product and the combustion feed to heat the first pyrolysis reactor.
43. The apparatus of any one of paragraphs 39 to 40, further comprising one or more lines providing fluid communication between the separation unit and the first pyrolysis reactor, at least one line being configured to combine a portion of the hydrogen product with the first pyrolysis feed.
44. The apparatus of any one of paragraphs 39 to 40, further comprising (i) one or more lines providing fluid communication between the separation unit and the first pyrolysis reactor, at least one of which being configured to provide a first portion of the hydrogen product to a combustion feed being provided to the first pyrolysis reactor and (ii) one or more lines providing fluid communication between the separation unit and the first pyrolysis reactor, at least one of which being configured to combine a second portion of the hydrogen product with the first pyrolysis feed.
45. The apparatus of any one of paragraphs 37 to 44, further comprising providing≥25.0 wt % of the hydrogen product to the converter, based on the weight of the hydrogen product.
46. The apparatus of any one of paragraphs 34 to 45, wherein the first pyrolysis reactor is configured to expose the first pyrolysis feed to the peak pyrolysis gas temperature from 1540° C. to 1800° C., and maintain the at least a portion of the first pyrolysis feed within the first pyrolysis reactor for a residence time between 0.5 second and 0.001 second.
47. The apparatus of any one of paragraphs 34 to 46, wherein the first pyrolysis reactor comprises at least one regenerative reverse flow reactor, the regenerative reverse flow reactor comprising: a reactor body, wherein the reactor body forms a reaction region within the reactor body; a packing material disposed at least partially within the reaction region; and one or more poppet valve assemblies coupled to the reactor body and in flow communication with the reaction region, at least one of the assemblies being configured to control fluid flow of the at least a portion of the first pyrolysis feed between a location external to the reactor body and within the reaction region.
48. The apparatus of any one of paragraphs 34 to 47, further comprising a feed separation unit in fluid communication with the at least one of the first pyrolysis reactor, the second pyrolysis reactor and a combination thereof, the feed separation unit being configured to separate a hydrocarbon feed into the first pyrolysis feed and second pyrolysis feed.
49. The apparatus of any of paragraphs 34 to 48, wherein the first pyrolysis reactor comprises a partial oxidation reactor.
50. The apparatus of any of paragraphs 34 to 48, wherein the first pyrolysis reactor comprises an arc reactor.
51. The apparatus of any of paragraphs 34 to 48, wherein the first pyrolysis reactor comprises a thermal pyrolysis reactor.
52. The apparatus of any one of paragraphs 34 to 51, wherein the second pyrolysis reactor operates at low-severity operating conditions to produce the second reactor product.

53. The apparatus of any one of paragraphs 34 to 51, wherein the second pyrolysis reactor operates at high-severity operating conditions to produce the second reactor product.

54. The apparatus of any one of paragraphs 34 to 48, wherein the first pyrolysis reactor is a regenerative reverse flow thermal pyrolysis reactor and the second pyrolysis reactor is a steam cracking thermal pyrolysis furnace.

While the present invention has been described and illustrated with respect to certain embodiments, it is to be understood that the invention is not limited to the particulars disclosed and extends to all equivalents within the scope of the claims.

The invention claimed is:

1. A hydrocarbon conversion method comprising:
providing a hydrocarbon feed comprising hydrocarbon and an added diluent, wherein the added diluent is added to the hydrocarbon feed in an amount more than zero but up to 10 wt % based on the combined weight of the hydrocarbons and the added diluent, and wherein the diluent is one or more of $H_2O$, $CO_2$, and $H_2S$;
separating the hydrocarbon feed into a first pyrolysis feed comprising methane and the added diluent; and a second pyrolysis feed comprising $C_{2+}$ fractions;
exposing the first pyrolysis feed in a first pyrolysis reactor to a peak pyrolysis gas temperature $\geq 1540°$ C., for a residence time of $\leq 50$ milliseconds, and at a pressure $\geq 36$ psig to produce a first reactor product comprising ethylene and acetylene, wherein the first reactor product has a $C_{3+}$: acetylene weight ratio that is $\leq 0.5$ and an ethylene to acetylene weight ratio that is $\geq 0.04$;
exposing the second pyrolysis feed to pyrolysis conditions in a second pyrolysis reactor to produce a second reactor product comprising ethylene and acetylene, wherein the first and second pyrolysis reactors are of different type; and
combining at least a portion of the first reactor product and at least a portion of the second reactor product to form a combined reactor product; wherein the first and second pyrolysis feeds comprise hydrocarbons, the hydrocarbons are derived from the hydrocarbon feed, and the hydrocarbon feed has a hydrogen content in a range of from 8 wt % to 20 wt %.

2. The method of claim 1, wherein the first reactor product has a $C_{3+}$ to acetylene weight ratio $\leq 0.45$, and wherein the added diluent is $CO_2$.

3. The method of claim 1, further comprising compressing at least one of (i) the at least a portion of the first reactor product or (ii) the at least a portion of the second reactor product prior to forming the combined reactor product.

4. The method of claim 1, further comprising converting at least a portion of the combined reactor product into a conversion product comprising ethylene and propylene.

5. The method of claim 4, further comprising polymerizing at least a portion of the conversion product into one or more of polyethylene and polypropylene.

6. The method of claim 1, further comprising separating hydrogen from one or more of the at least a portion of the first reactor product, the at least a portion of the second reactor product and the combined reactor product.

7. The method of claim 6, further comprising passing at least a portion of the separated hydrocarbon to one or more of the first pyrolysis feed and the second pyrolysis feed.

8. The method of claim 6, further comprising (i) combining a combustion feed with a first portion of the separated hydrogen from one or more of the first pyrolysis reactor and the second pyrolysis reactor and reacting the combustion feed along with the first portion of the separated hydrogen and (ii) passing at least a portion of the separated hydrogen to one or more of the first pyrolysis feed and the second pyrolysis feed.

9. The method of claim 6, further comprising combining at least a portion of the separated hydrogen with the combined reactor product to form a mixture, and providing the mixture to an acetylene converter unit utilized to convert at least a portion of the mixture to an ethylene product.

10. The method of claim 1, wherein the peak pyrolysis gas temperature is in the range of 1600.0° C. to 1800.0° C.

11. The method of claim 1, further comprising:
exothermically reacting a first combustion feed with a second combustion feed to heat a region at least partially within the first pyrolysis reactor;
removing combustion products from the first pyrolysis reactor; and
heating the first pyrolysis feed using at least a portion of the heat generated by the exothermic reaction.

12. The method of claim 1, wherein the first pyrolysis reactor is a regenerative reverse flow thermal pyrolysis reactor and the second pyrolysis reactor is a steam cracking thermal pyrolysis furnace.

13. A hydrocarbon conversion method comprising:
providing a hydrocarbon feed comprising hydrocarbon and an added diluent, wherein the added diluent is added to the hydrocarbon feed in an amount more than zero but up to 10 wt % based on the combined weight of the hydrocarbons and the added diluent, and wherein the diluent is one or more of $H_2O$, $CO_2$, and $H_2S$;
separating the hydrocarbon feed into a first pyrolysis feed comprising methane and the added diluent and a second pyrolysis feed, the second pyrolysis feed comprising $C_{2+}$ fractions;
exposing the first pyrolysis feed in a first pyrolysis reactor to a peak pyrolysis gas temperature $\geq 1540°$ C., for a residence time of $\leq 50$ milliseconds, and at a pressure $\geq 36$ psig to produce a first reactor product comprising ethylene and acetylene, wherein the first reactor product has a $C_{3+}$: acetylene weight ratio that is $\leq 0.5$ and an ethylene to acetylene weight ratio that is $\geq 0.04$;
exposing the second pyrolysis feed to pyrolysis conditions in a second pyrolysis reactor to produce a second reactor product comprising ethylene and acetylene, wherein the first and second pyrolysis reactors are of different type; and
combining at least a portion of the first reactor product and at least a portion of the second reactor product to form a combined reactor product; wherein the first and second pyrolysis feeds comprise hydrocarbons, the hydrocarbons are derived from the hydrocarbon feed, and the hydrocarbon feed has a hydrogen content in the range of $\leq 20$ wt %.

14. The method of claim 13, wherein the added diluent is $CO_2$, the first pyrolysis feed has a hydrogen content of between 6 wt % to 12 wt %, the pressure in the first reactor during the pyrolysis is $\geq 44$ psig, the peak pyrolysis gas temperature in the first reactor during the pyrolysis is $\geq 1650°$ C., and the first reactor product has an ethylene to acetylene weight ratio that is $\geq 0.05$.

* * * * *